(12) United States Patent
Pfenniger et al.

(10) Patent No.: US 7,713,461 B2
(45) Date of Patent: *May 11, 2010

(54) PROCESS FOR PRODUCING AN ORAL CARE DEVICE

(75) Inventors: Philipp Pfenniger, Triengen (CH); Franz Fischer, Triengen (CH); Beat Huber, Buron (CH)

(73) Assignee: Trisa Holding AG, Triengen (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/802,519

(22) Filed: May 23, 2007

(65) Prior Publication Data

US 2007/0222109 A1 Sep. 27, 2007

Related U.S. Application Data

(63) Continuation-in-part of application No. 10/318,086, filed on Dec. 13, 2002, now Pat. No. 7,240,390.

(30) Foreign Application Priority Data

Sep. 27, 2002 (DE) ................................. 102 45 086

(51) Int. Cl.
*B29C 45/14* (2006.01)
(52) U.S. Cl. ............................. 264/272.21; 264/272.11; 264/271.1; 264/259; 15/22.1
(58) Field of Classification Search ................. 264/239, 264/241, 259, 271.1, 272.11, 272.21; 15/22.1
See application file for complete search history.

(56) References Cited

U.S. PATENT DOCUMENTS

| 3,135,881 A | 6/1964 | Fresard |
| 3,346,748 A | 10/1967 | McNair |
| 3,358,309 A | 12/1967 | Richardson |
| 3,685,080 A | 8/1972 | Hubner |
| 3,779,238 A | 12/1973 | Cutler et al. |
| 3,967,617 A | 7/1976 | Krolik |
| 4,027,348 A | 6/1977 | Flowers et al. |
| 4,341,992 A * | 7/1982 | Goldstein ................... 324/693 |
| 4,837,892 A | 6/1989 | Lo |
| 5,033,150 A | 7/1991 | Gross et al. |

(Continued)

FOREIGN PATENT DOCUMENTS

CN          2087500 U       10/1991

(Continued)

*Primary Examiner*—Joseph S Del Sole
*Assistant Examiner*—Stephen Sollenberger
(74) *Attorney, Agent, or Firm*—Oliff & Berridge, PLC

(57) ABSTRACT

The invention relates to a process for producing an oral care device, such as a toothbrush, having a body, which comprises a handle region, a head region and a neck region located between the handle region and the head region, and having functional elements which are arranged, at least in part, within the body and comprise an electrically operated functional unit and an electric supply device which has an energy store and is intended for the functional unit, in the case of which the body is produced, by injection molding, from at least one hard component, which serves as a reinforcement, and at least one soft component, and at least some of the functional elements, during the production of the body, are encapsulated, at least in part, directly by the plastic which forms the soft component.

34 Claims, 16 Drawing Sheets

U.S. PATENT DOCUMENTS

| | | | |
|---|---|---|---|
| 5,046,249 | A | 9/1991 | Kawara et al. |
| 5,058,230 | A | 10/1991 | Hodush et al. |
| 5,071,348 | A | 12/1991 | Woog |
| 5,123,841 | A | 6/1992 | Millner |
| 5,138,733 | A | 8/1992 | Bock |
| 5,165,131 | A | 11/1992 | Staar |
| 5,253,382 | A | 10/1993 | Beny |
| 5,267,579 | A | 12/1993 | Bushberger |
| 5,353,460 | A | 10/1994 | Bauman |
| 5,372,501 | A | 12/1994 | Shalvi |
| 5,394,584 | A | 3/1995 | Breitschmid |
| 5,435,033 | A | 7/1995 | Millner |
| 5,471,695 | A | 12/1995 | Aiyar |
| 5,511,270 | A | 4/1996 | Eliachar et al. |
| 5,546,624 | A | 8/1996 | Bock |
| 5,574,253 | A | 11/1996 | Golob et al. |
| 5,590,434 | A | 1/1997 | Imai |
| 5,613,259 | A * | 3/1997 | Craft et al. .................... 15/22.1 |
| 5,622,192 | A | 4/1997 | Chiou |
| 5,706,541 | A | 1/1998 | Gutelius et al. |
| 5,718,667 | A | 2/1998 | Sugimoto et al. |
| 5,735,012 | A | 4/1998 | Heinzelman et al. |
| 5,822,821 | A * | 10/1998 | Sham ......................... 15/22.1 |
| 5,876,207 | A | 3/1999 | Sundius et al. |
| 5,894,453 | A | 4/1999 | Pond |
| 5,987,681 | A | 11/1999 | Hahn et al. |
| 6,029,304 | A | 2/2000 | Hulke et al. |
| 6,036,908 | A | 3/2000 | Nishida et al. |
| 6,058,542 | A | 5/2000 | Lo |
| 6,105,191 | A | 8/2000 | Chen et al. |
| 6,108,869 | A | 8/2000 | Meessmann et al. |
| 6,202,242 | B1 * | 3/2001 | Salmon et al. ............... 15/22.1 |
| 6,298,516 | B1 | 10/2001 | Beals et al. |
| 6,319,448 | B1 | 11/2001 | Kirchdoerffer et al. |
| 6,389,633 | B1 | 5/2002 | Rosen |
| 6,412,137 | B1 | 7/2002 | Heidari |
| 6,425,295 | B1 | 7/2002 | Meginnis |
| 6,802,097 | B2 * | 10/2004 | Hafliger et al. .............. 15/22.1 |
| 2001/0013152 | A1 | 8/2001 | Meyer et al. |
| 2001/0034006 | A1 | 10/2001 | Lang et al. |
| 2002/0100134 | A1 | 8/2002 | Dunn et al. |
| 2002/0120991 | A1 | 9/2002 | Cacka et al. |
| 2002/0124333 | A1 | 9/2002 | Hafliger et al. |
| 2002/0178519 | A1 | 12/2002 | Zarlengo |
| 2003/0196283 | A1 | 10/2003 | Eliar et al. |
| 2003/0226223 | A1 | 12/2003 | Chan |
| 2004/0060134 | A1 | 4/2004 | Eliar et al. |
| 2004/0060135 | A1 | 4/2004 | Gatzemeyer et al. |
| 2004/0060136 | A1 | 4/2004 | Gatzemeyer et al. |
| 2006/0026780 | A1 | 2/2006 | Hafliger et al. |

FOREIGN PATENT DOCUMENTS

| | | |
|---|---|---|
| DE | 2820437 | 7/1979 |
| DE | 37 24 476 A1 | 1/1989 |
| DE | 40 32 779 C2 | 4/1992 |
| DE | 44 36 523 A1 | 4/1996 |
| EP | 704180 | 3/1996 |
| EP | 0 910 258 B | 4/1999 |
| GB | 2 243 569 A | 11/1991 |
| GB | 2 250 428 A | 10/1992 |
| JP | A 03-222905 | 1/1991 |
| JP | A 07-327737 | 12/1995 |
| WO | WO 98/01055 A1 | 1/1998 |
| WO | WO 99/59462 | 11/1999 |
| WO | WO 99/63859 | 12/1999 |
| WO | WO 00/07482 | 2/2000 |
| WO | WO 01/28452 A1 | 4/2001 |
| WO | WO 01/47392 A1 | 7/2001 |
| WO | WO 01/58306 A1 | 8/2001 |
| WO | WO 02/054906 A1 | 7/2002 |
| WO | WO 02/062174 A1 | 8/2002 |

* cited by examiner

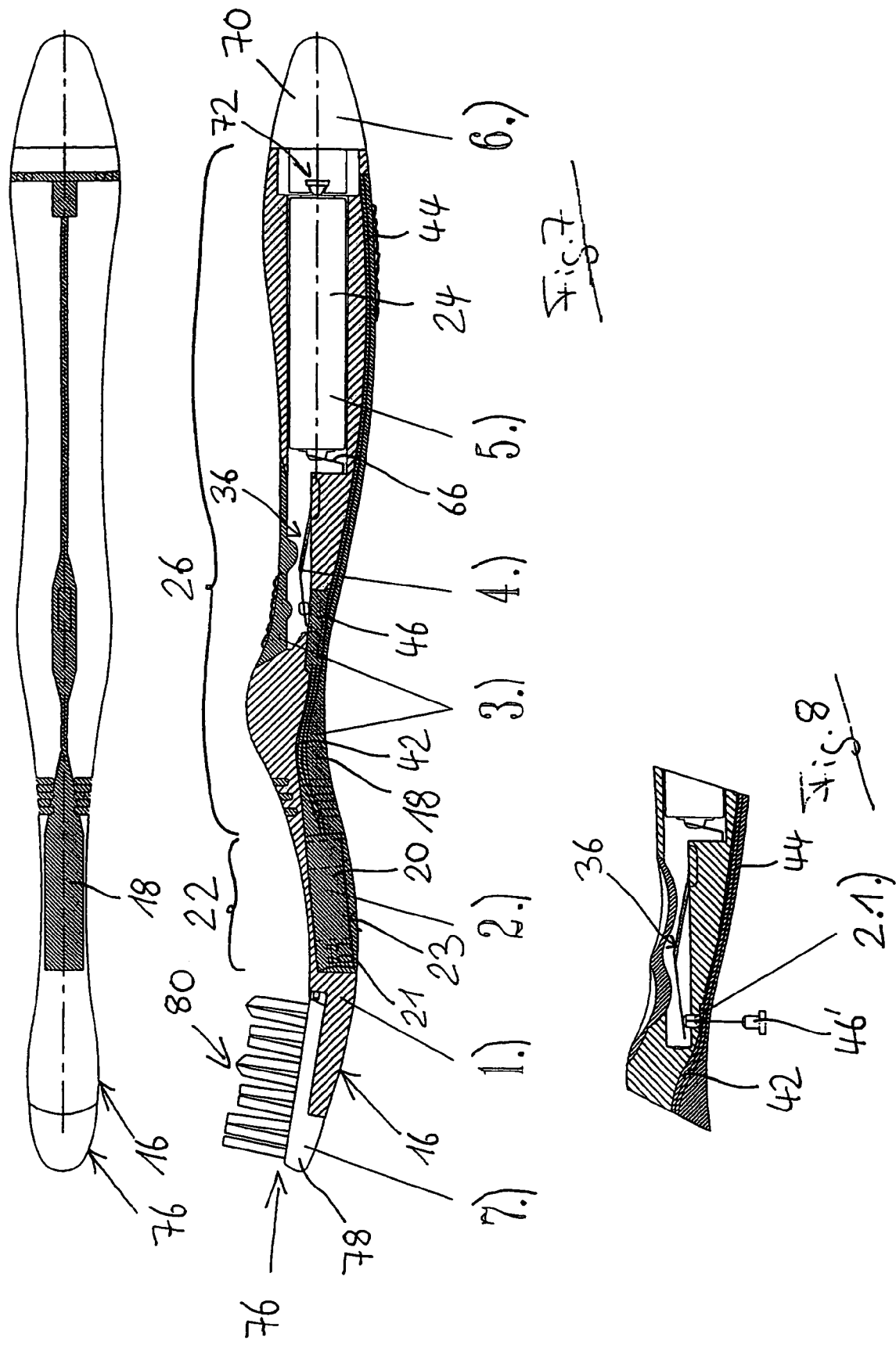

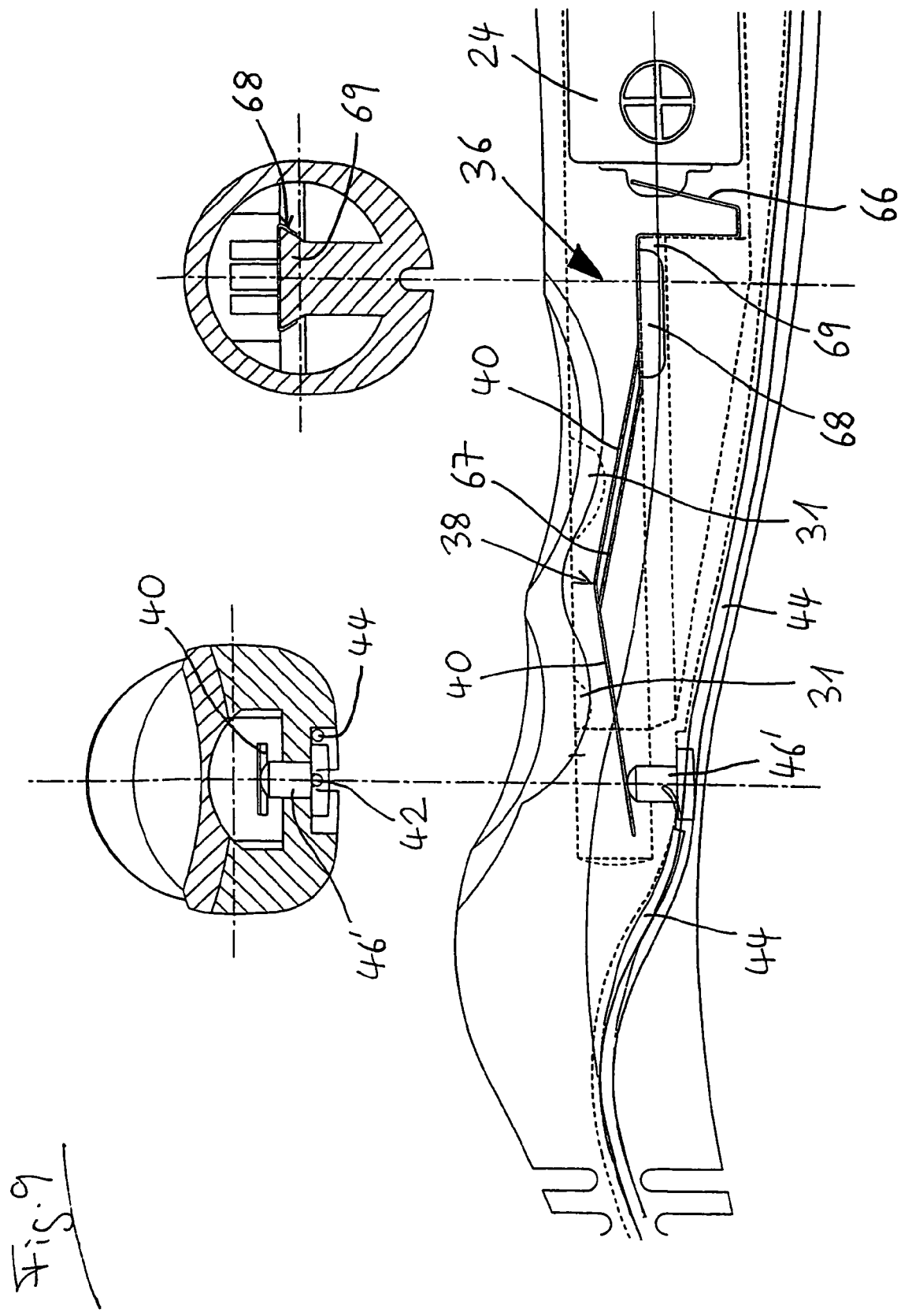

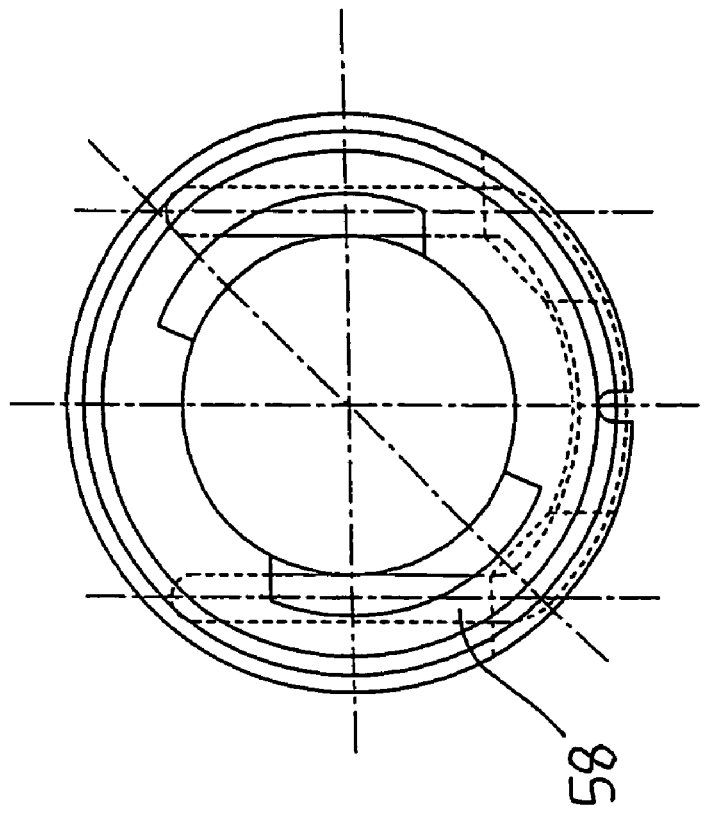
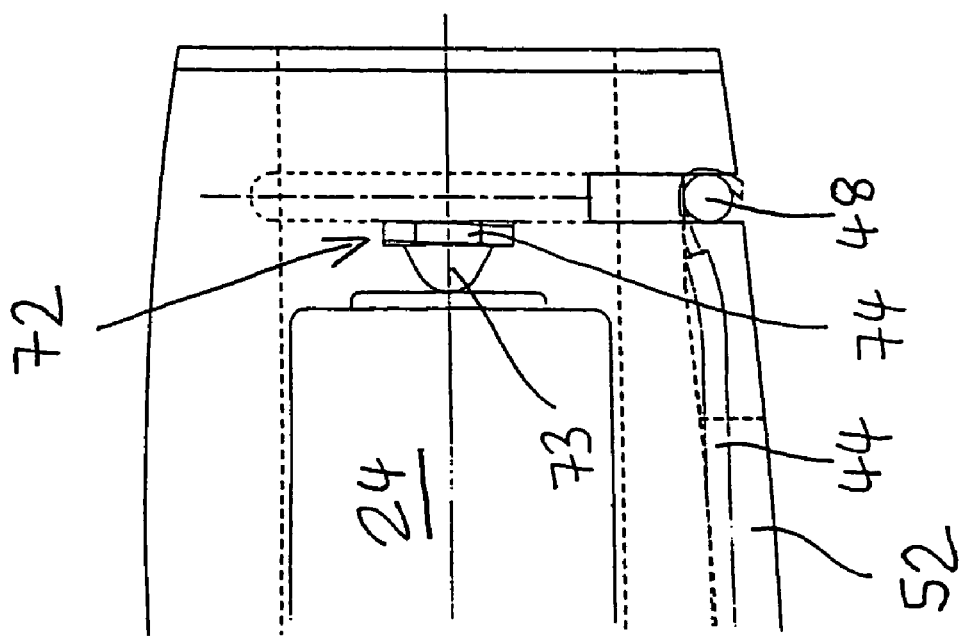
Fig. 10

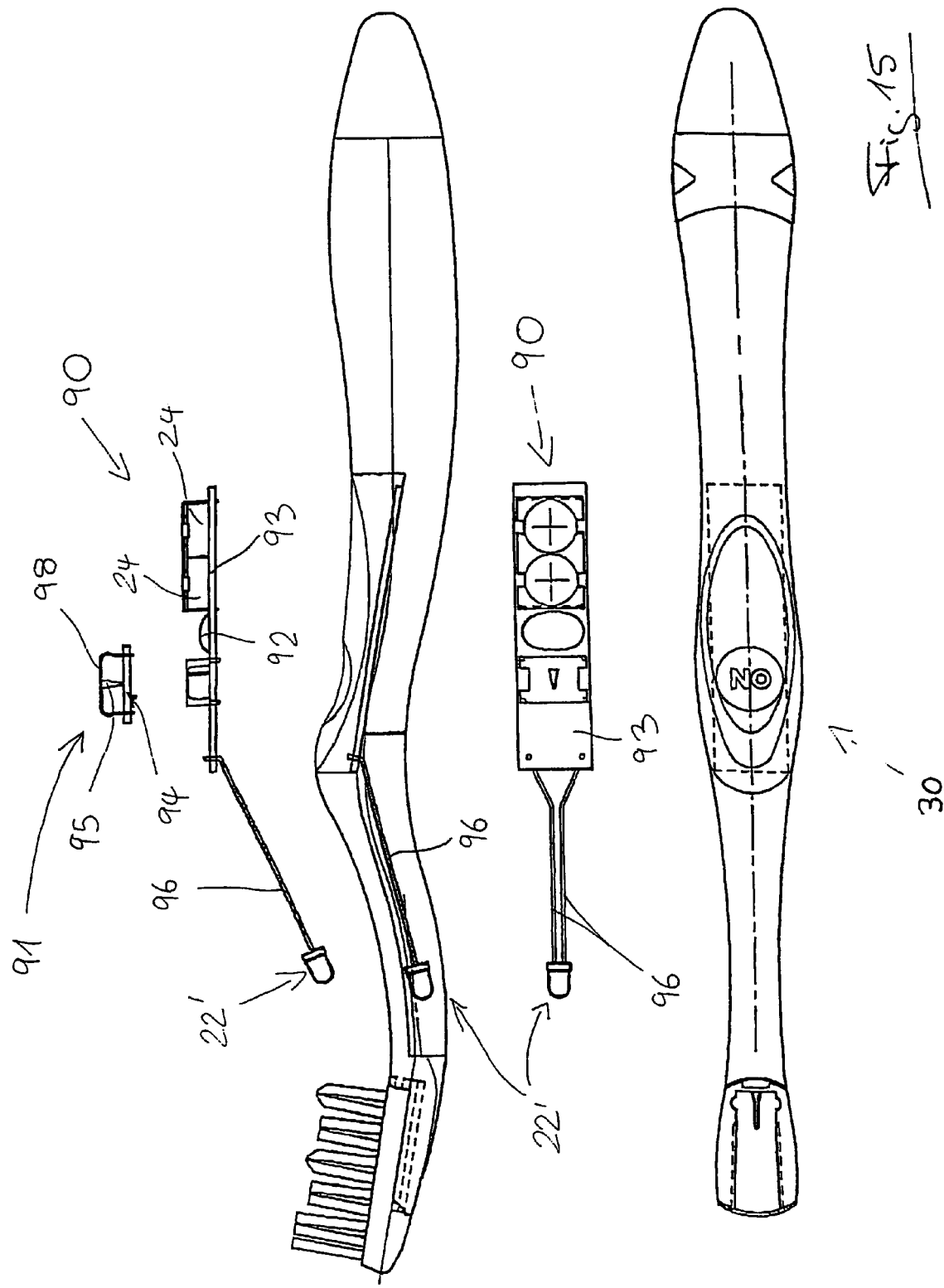

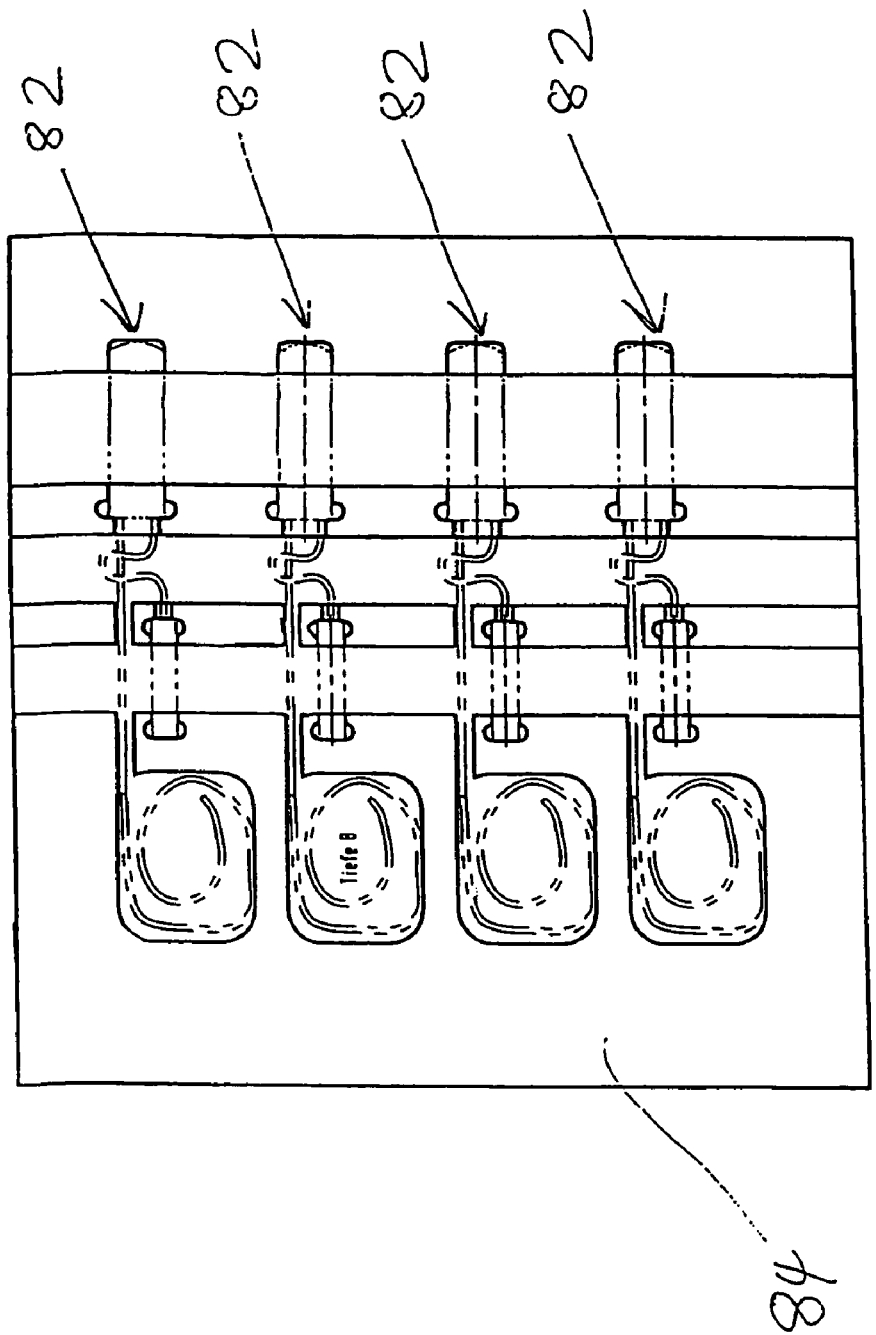

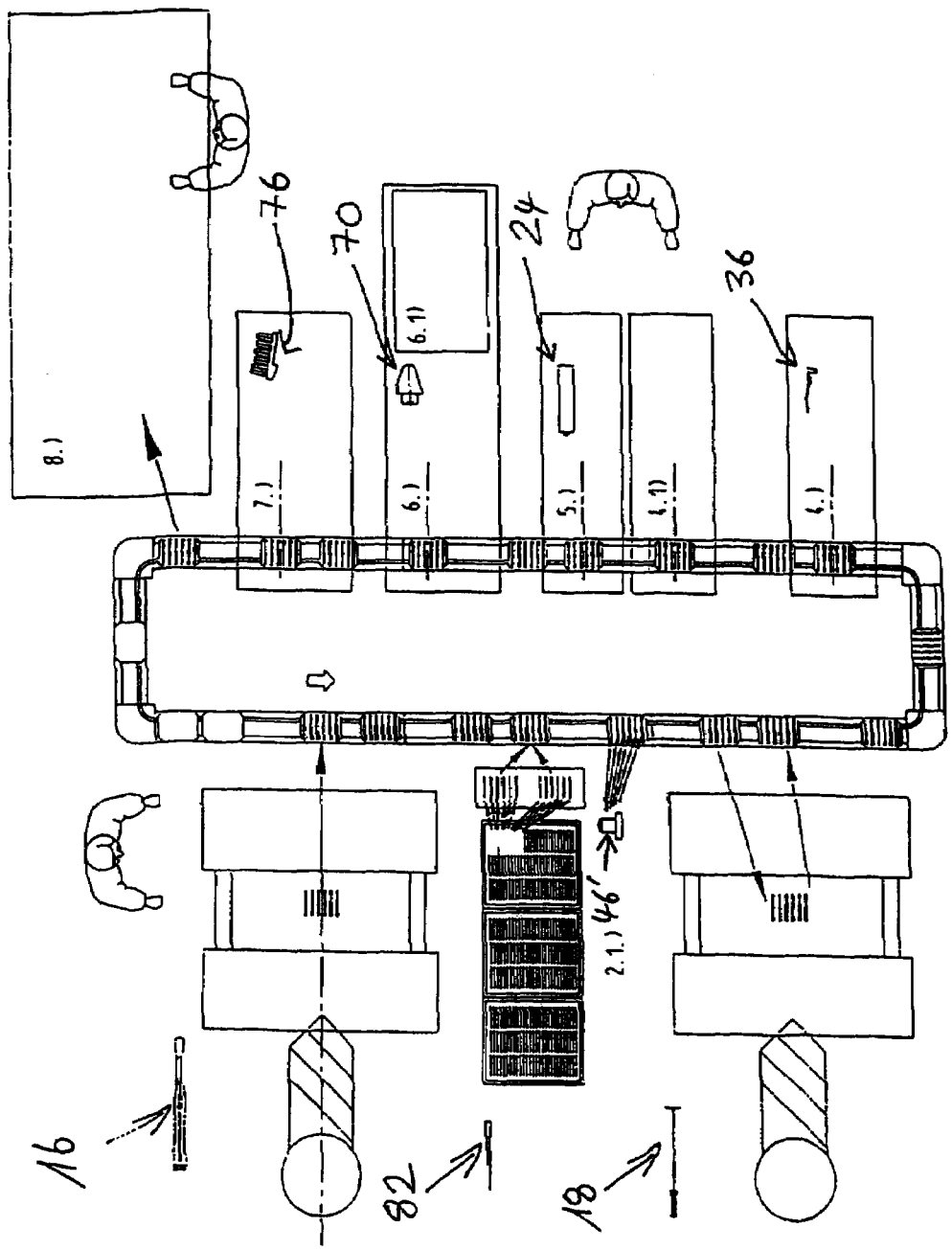

PROCESS FOR PRODUCING AN ORAL CARE DEVICE

CROSS-REFERENCE TO RELATED APPLICATION

This application is a Continuation-in-Part of application Ser. No. 10/318,086 filed Dec. 13, 2002.

BACKGROUND OF THE INVENTION

1. Field of Invention

The invention relates to a process for producing an oral care device, such as a toothbrush having a body, which comprises a handle region, a head region and a neck region located between the handle region and the head region, and having functional elements which are arranged, at least in part, within the body and comprise an electrically operated functional unit and an electric supply device which has an energy store and is intended for the functional unit.

2. Description of Related Art

Such oral care devices in the form of toothbrushes are known in principle. WO 99/63859 A1 describes a toothbrush in the case of which, according to one embodiment, an LED and a switching unit for switching the LED on and off are integrated in a toothbrush handle designed as a light guide, the switching unit comprising a battery, a flexible contact electrode and a flexible membrane. In the region of the membrane of the switching unit, the material of the toothbrush handle has a thin material layer formed over it in order to form a projecting region.

WO 00/07482 A1 concerns the detection of deposits on the teeth. A description is given of a toothbrush in which light-guiding elements are integrated. In this case, the light-guiding elements are integrated in the toothbrush head, which is produced, by injection molding, separately from the toothbrush handle and is then coupled to the toothbrush handle.

WO 99/59462 A1 likewise deals with the detection of deposits on the teeth. In this context, the document also describes a toothbrush with integrated light-guiding elements, although in this document the toothbrush merely plays a minor role.

WO 01/47392 A1 describes a toothbrush which is provided with means which make it possible to establish and monitor the tooth-brushing technique when using the toothbrush.

During the production of such toothbrushes the particular concern is for the functional elements arranged within the body to be positioned correctly and for reliable functioning to be ensured. Since such toothbrushes are mostly produced in large numbers, it is further intended for production to be possible within the framework of cost-effective and efficient mass production. Since, furthermore, the outer appearance of the toothbrush increasingly plays a not inconsiderable part in the decision-making process for buying a toothbrush, the greatest possible freedom of design in respect of the toothbrush is to be possible, and this has to be taken into account during the production of the toothbrush. It is not just a question here of creating an ergonomically advantageous toothbrush which is easy to hold; rather, it is also necessary for the toothbrush to be easy to use, to be capable of being held securely during use and to have a satisfactory surface with a pleasant feel, i.e. the intention is for the user simply to want to pick up the toothbrush.

The toothbrush production described in WO 01/58306 A1 involves comparatively high outlay since use is made of two separate half-shells in the case of which problems may arise in respect of the shells warping and thus of the accuracy of fit and the water-tightness. Furthermore, a plurality of injection molds or a plurality of different cavities are necessary for the shells, on the one hand, and the additionally necessary encapsulation, on the other hand. Moreover, the operation of fitting the functional elements is associated with relatively high outlay.

In the case of the production process described in WO 02/054906 A1, there are only limited design possibilities since use is made of a mold core which is removed following the injection-molding operation, as a result of which the shaping is restricted to essentially cylindrical geometries. In particular, it is only possible to produce toothbrushes with a straight neck region, in order to allow the components to be pushed in from the rear.

WO 01/28452 A1 describes the production of a toothbrush by injection molding with two or more components. A vibration arrangement, connecting lines and further electronic components are positioned as a unit here in a molding injection molded from a first material component, and are then encapsulated by the second material component—or by the further material components—although there is no need for full encapsulation here. Some parts may be exposed, as a result of which it is possible to achieve an aesthetic effect. No further details relating to the injection-molding process or to the material components are given in this document.

SUMMARY OF THE INVENTION

An object of an embodiment of the invention is to make it possible to produce oral care devices, such as toothbrushes, which satisfy the requirements mentioned in the introduction and in the case of which in embodiments, along with a minimum number of necessary injection molds and assembly steps, maximum freedom of design is achieved at the same time, it being intended, in embodiments, for the production of curved neck regions to be possible.

According to aspects of the invention, a body is produced, by injection molding, from at least one hard component, which serves as a reinforcement, and at least one soft component, and in that, during the production of the body, some of the functional elements are encapsulated, at least in part, directly by the plastic which forms the soft component.

Producing an oral care device body, such as a toothbrush body, from at least one hard component and at least one soft component allows a high level of design freedom, with the stability and strength requirements which are to be met by the oral care device being satisfied at the same time.

By virtue of the operation, provided according to the invention, of the functional elements being encapsulated directly by the plastic, the functional elements are integrated in optimal fashion in the oral care device body. It is thus possible, even during the production of the body, for the functional elements to be positioned in the body at the locations appropriate for the respective design, as a result of which the designer has maximum freedom for configuring the toothbrush. Furthermore, the oral care device production is shortened and simplified to a considerable extent by the procedure according to the invention since injection-molding and assembly steps take place at the same time. Furthermore, it is advantageous that the functional parts are automatically fixed on the oral care device body by being encapsulated directly by the plastic, which simplifies the task of carrying out further production steps which may possibly be necessary.

It is particularly advantageous, moreover, that the functional elements may be protected in optimal fashion against external influences as a result of the encapsulation and may be encapsulated, in particular, in a water-tight manner.

The invention is a departure from the known toothbrush-production procedure, in the case of which injection-molding steps, on the one hand, and assembly steps, on the other hand, are kept very much separate. It has been found according to the invention that, in principle, the functional elements may be subjected to the pressure and temperature loading occurring during plastic injection molding without the functional capability of the elements being adversely affected.

The invention also relates to an oral care device, such as a toothbrush, in the case of which at least some functional elements are encapsulated, at least in part, directly by the plastic which forms the toothbrush body.

Preferred embodiments of the invention are specified in the dependent claims, the description and the drawing.

For example, it is preferably the case that first of all precisely one hard component is injection molded and then precisely one soft component is injection molded. Alternatively, it is also possible for precisely two soft components to be injection molded.

In a particularly preferred variant of the production process according to the invention, first of all a first, preferably hard, component is injection molded without functional elements, whereupon at least some functional elements are positioned, and fixed, on the first component, the unit comprising first component and functional elements subsequently being encapsulated, at least in part, by at least one further, preferably soft, component. It is advantageous in the case of this variant that there is no need for any specific measures to be taken in order for the functional elements which are to be encapsulated to be secured on the injection mold. In particular when the first injection-molded component is a hard component and the further injection-molded component is a soft component, this variant provides the further advantage of the functional elements which are to be encapsulated by the soft component being subject to particularly gentle treatment since, at least in most cases, soft components may be injection molded at a low pressure and low temperature in comparison with the hard component.

According to an alternative variant, prior to the injection molding of a first component, at least some functional elements are positioned in an injection mold, and are then encapsulated by the first component, the unit comprising first component and encapsulated functional elements subsequently being encapsulated by at least one further component. Since, in the case of this variant, the functional elements are first of all positioned on the injection mold and the mold thus has to act on the functional elements in order to retain the same, the first component, once injection molded, is provided with clearances for the points of engagement on the previously positioned functional elements. These clearances are closed during the injection molding of the further component, with the result that they are no longer visible on the finished product.

In order further to minimize the loading to which the functional elements are subjected by the injection molding, a further exemplary embodiment of the invention may provide that, at least in the case of one component, first of all, in a first step, the functional elements are covered over at a low injection pressure and then, in at least one further step, the component is completed at a high injection pressure.

It is further preferably provided according to the invention that, prior to the injection molding of a further component, the unit comprising at least one first component and functional elements which are to be encapsulated has fixed on it at least one further functional element which is to be encapsulated. This further functional element is, in particular, a, for example, pin-like, clamp-like or clip-like contact element for producing an electrical connection between two or more other functional elements.

The functional elements may advantageously be used for an additional purpose if, according to a further preferred embodiment of the invention, at least one cavity of a first component, the cavity being provided for one or more functional elements which are to be inserted at a later stage, is sealed in relation to a further component by at least one functional element which is encapsulated by the first component and/or is to be encapsulated by at least one further component.

A further preferred exemplary embodiment of the invention provides that injection molding a soft component forms an actuating region, which can be pressed into a cavity of a previously injection-molded hard component for the purpose of actuating at least one electrical functional element. This advantageously uses the elastic properties of the soft component in order to provide an actuating region, for example, for acting on a switching element which is arranged in the toothbrush body and is intended for switching the toothbrush on and off.

It is further proposed according to the invention to produce a vibration-damping region of the body, which is located, in particular, in the neck region or in the region of the transition between the neck region and handle region, from at least two different injection-molded components. This makes it possible for the damping properties of the damping region to be adapted specifically to the respective requirements. It is particularly preferred if the vibration-damping region is formed by specific weakening of a hard component by means of a soft component.

In order to form the vibration-damping region, it is preferred if first of all, during the injection molding of a hard component, the latter is produced with a pattern of recesses and then, during the injection molding of at least one further component, in particular a soft component, the recesses are filled by the latter.

An electrical connection between, on the one hand, a vibration device arranged in the head region or in the neck region and, on the other hand, an energy store arranged in the handle region can preferably be produced or broken via a bistable switching element, which can be changed over between two at least essentially dimensionally stable states by activation of two legs located on opposite sides of an articulation region.

Such a bistable switching element, which is also referred to as a "butterfly", can be actuated, in particular, by a switching region which is formed by an injection-molded soft component and is pressed, by the user, into a cavity in which the butterfly is arranged.

The functional elements which are encapsulated directly by at least one plastic component are as follows:
 a vibration device, which preferably comprises an arrangement made up of an electric motor and eccentric or an electrically driven vibratory armature,
 electric lines connected to the vibration device, and
 separate contact elements which serve for producing electrical connections between the other functional elements.

It is also possible, in principle, for the functional elements which are to be encapsulated to comprise—in dependence on the respective design of the toothbrush—sensors (e.g. sensors for measuring pressure and time, for detecting plaque, for determining positions, for establishing positions, for establishing movement and for detecting chemical substances or compounds), light-emitting elements, resistors, ICs, switching devices and acoustic components. The functional elements may thus be electronic components which may have a comparatively high level of sensitivity in relation to external influences. The functional elements may be provided with a protective sheath, for example made of plastic, ceramic material or metal. It is also possible for the functional elements to be encapsulated by a resin or some other protective material.

In order for the loading to which the functional elements which are to be encapsulated are subjected to be reduced to a minimum, it is preferred according to the invention if use is made of a relatively low injection pressure, although homogeneous material distribution in the respective injection molding is ensured at the same time. Plastics which flow particularly easily are preferably used. The material which is preferred according to the invention is PP MVR 4-25, use being made, in particular, of PP with a melt flow index of MVR 20.

Furthermore, relatively low processing temperatures are preferably provided according to the invention. In particular when, according to the particularly preferred variant mentioned above, first of all a first component is injection molded without functional elements, the preferred material to use is TPE, to be precise at a temperature in the range of from 170° C. to 250° C., preferably approximately 200° C.

It is possible according to the invention, during the injection molding of the components, to use in each case either a single injection point or a plurality of injection points. In the case of a single injection point, the position of the latter is preferably selected such that the most sensitive functional element is located at the greatest possible distance from the injection point, with the result that it is necessary to cover the longest possible plastic-filling distance to the functional element. If use is made both of a single injection point and of a plurality of injection points, it is also possible to work in each case with an injection pressure which varies over time. The pressure profile here may be adapted specifically to the respective conditions. In particular at the injection point located nearest to the most sensitive functional element, it is possible to work with a relatively low holding pressure of less than 600 bar, and preferably of less than 200 bar.

As far as the plastic materials used are concerned, use may be made, for example, of ABS, PET, SAN, PC, PA or PMMA for a hard component of the toothbrush body, the preferred material being PP. For the soft component, use is preferably made of a TPE which has an affinity for the respective hard component, as a result of which it is possible to achieve particularly suitable flexible and/or elastomeric properties.

It is possible to provide a transparent or at least translucent plastic for at least one component of the oral care device body. MABS, SAN, PA, PC, PMMA or PET, in particular, are possible for this purpose. During the processing of transparent plastics, use is preferably made of a comparatively high injection pressure, for which purpose the abovementioned variant in the case of which first of all a first component is injected molded without functional elements is particularly suitable.

It is further preferably provided according to the invention that the wall thickness of the plastic does not fall below a predetermined minimum value either at any location or at least in such regions of the toothbrush body as are subjected to relatively large forces, in particular bending and torsional forces. In the case of the hard component, this minimum wall thickness preferably does not fall below a value of approximately 0.5 mm, the minimum wall thickness preferably being in the range of from 1 to 5 mm. A region at which the wall thickness goes down to the minimum value is preferably the region of the neck at which the vibration device is arranged.

A further preferred embodiment of the invention provides that at least some functional components are arranged on an already injection-molded plastic component, in particular a hard component, such that the functional elements, in relation to the direction of flow of a further plastic component, in particular a soft component, which is still to be injection molded, are located, at least in certain regions, in the shadow of at least one protected section of the hard component.

It is thus possible for the functional elements which are to be encapsulated to be protected in a particularly straightforward, and nevertheless effective, manner against the influences in particular of pressure and temperature of the component or components which is or are to be injected molded subsequently. The sections located upstream of the functional elements are, in particular, protrusions or obstructions, which are provided specifically or are present anyway as part of the design, of the previously injection-molded component.

Furthermore, the plastic body which is to be injection molded for the toothbrush according to the invention is preferably designed such that sharp protrusions, edges and corners are avoided in the region of the functional elements in order to eliminate, or at least reduce to a minimum, the risk of fracture caused, in particular, by a notch effect.

In order to supply functional elements with electrical energy, use is preferably made of electric lines in the form of a metallic wire which, at least when lines of different polarities are guided together, are preferably provided with an electrically insulating sheath. Such a sheath may be dispensed with, in particular, when the relevant lines are guided separately and at a sufficiently large distance apart from one another. It is alternatively possible to provide the electrical connections in the form of injection-molded, electrically conductive plastics, of punched metal plates, of conductor tracks embossed metallically on the injection-molded plastic component, or of conductor tracks applied to the injection-molded plastic component by electroplating.

Furthermore, preferably at least those electrical connections which are guided along such regions of the toothbrush, in particular the neck region, as are subjected to elastic deformation are configured such that, on the one hand, they are as flexible as possible and fracture-resistant in relation to alternating bending and, on the other hand, do not result in additional stiffening of the relevant toothbrush region.

The plastic body of the oral care device, such as a toothbrush, is preferably designed according to the invention such that electrical connections between a power source and a power-consuming unit run along as straight a line as possible. It is thus possible for electric lines to be removed particularly straightforwardly during assembly. For this purpose, an at least essentially straight channel for electric connecting lines is preferably formed in one of the injection-molded components of the toothbrush body.

BRIEF DESCRIPTION OF THE DRAWINGS

The invention is described hereinbelow, by way of example, with reference to the drawing, in which:

FIGS. 1-7 show individual steps of a process for producing a toothbrush according to one embodiment of the invention, FIG. 8 shows a step from an alternative production process according to the invention, FIG. 9 shows an enlarged illustration of the arrangement and functioning of a switching element of a toothbrush according to the invention, FIG. 10 shows an enlarged illustration of a possible way of producing an electrical connection in a toothbrush according to the invention, FIG. 15 shows various views of a further embodiment of a toothbrush according to the invention, FIG. 16 shows an example of a placement pallet which can be used in the case of a production process according to the invention, and FIG. 17 shows, schematically, an example of an assembly installation for the production according to the invention of a toothbrush according to the invention.

DETAILED DESCRIPTION OF PREFERRED EMBODIMENTS

The variant which will be described hereinbelow first of all with reference to FIGS. 1-8 relates to a particularly preferred production process according to the invention, in the case of which first of all a hard plastic component 16 of the toothbrush body is injection molded without functional elements.

Figure 1:
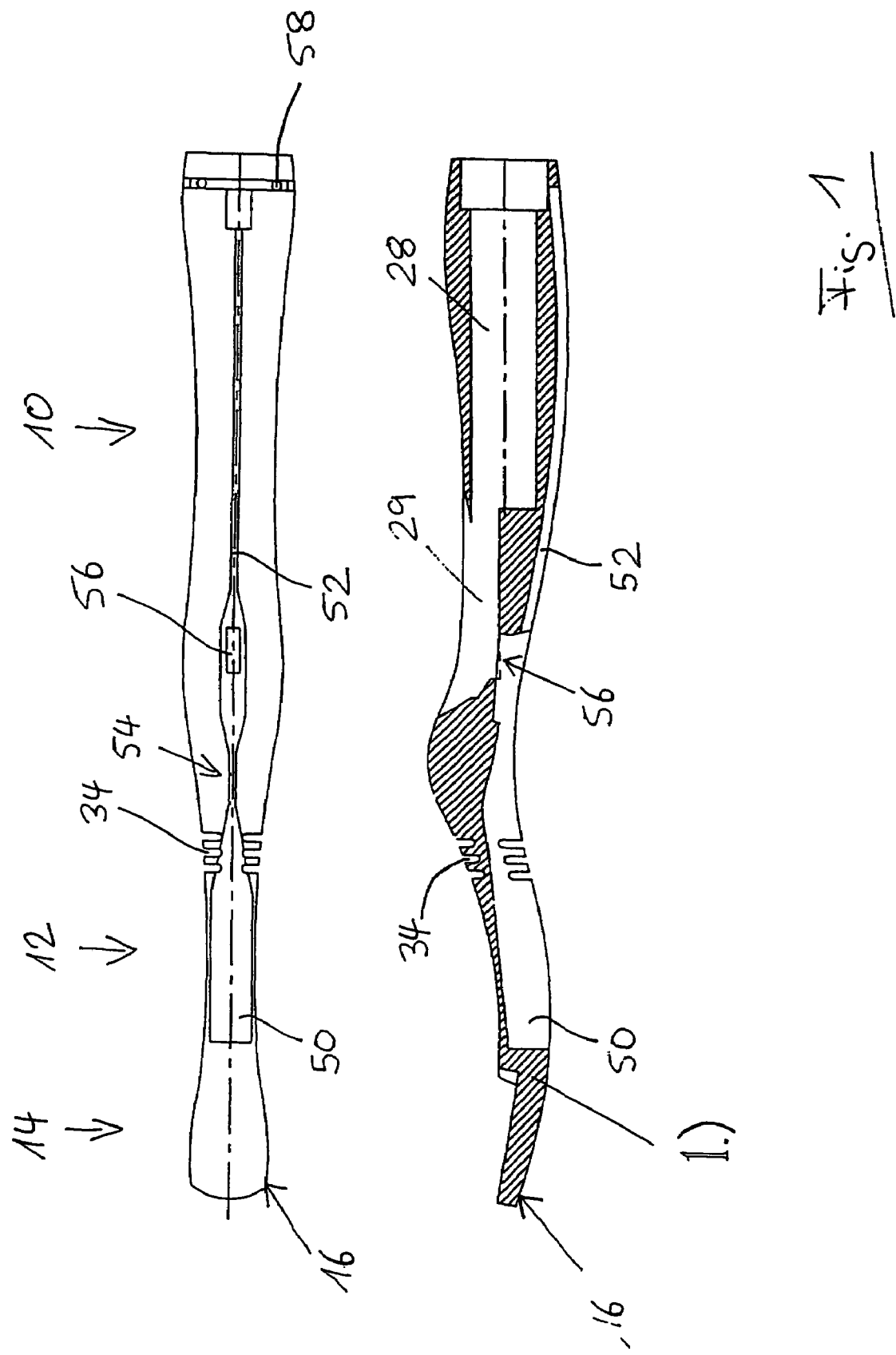

FIG. 1 shows the injection-molded hard component 16, in the case of which a handle region 10, a neck region 12 and a head region 14 have already been formed. The neck region 12, which spaces the head region 14 and the handle region 10 apart from one another, preferably has a length in the range of from 30 mm to 70 mm, in particular approximately 50 mm. The neck region 12, which connects the handle region 10 and the head region 14 to one another, is tapered in relation to the handle region 10 and the head region 14, as can be seen from the top part of FIG. 1, this top part showing the rear view.

The hard component 16 further comprises a recess 50, which is formed in the neck region 12 and is intended for a vibration device, recesses 34, which are formed in the transition region between the neck region 12 and handle region 10 and form a constituent part of a vibration-damping region 32, a channel 52, which extends from the front cavity 50 into the region of the rear end and is intended for electric connection lines, a rear cavity 28, which is intended for an energy store in the form of a battery or of a rechargeable storage battery of AAA type, and a cavity 29 for the actuation of a switching element (not illustrated). The cavity 29 is connected, via a through-passage 56, to the channel 52, which is widened in this region.

As can be gathered, in particular, from the bottom part, which illustrates a sectional side view, the channel 52 runs on the underside of the toothbrush.

The hard component 16 also has a recess 58 for a U-shaped contact clip in the region of the rear end.

The abovementioned features of the hard component 16 and the functional elements of the toothbrush according to the invention will be discussed in more detail elsewhere in the text.

Figure 2:
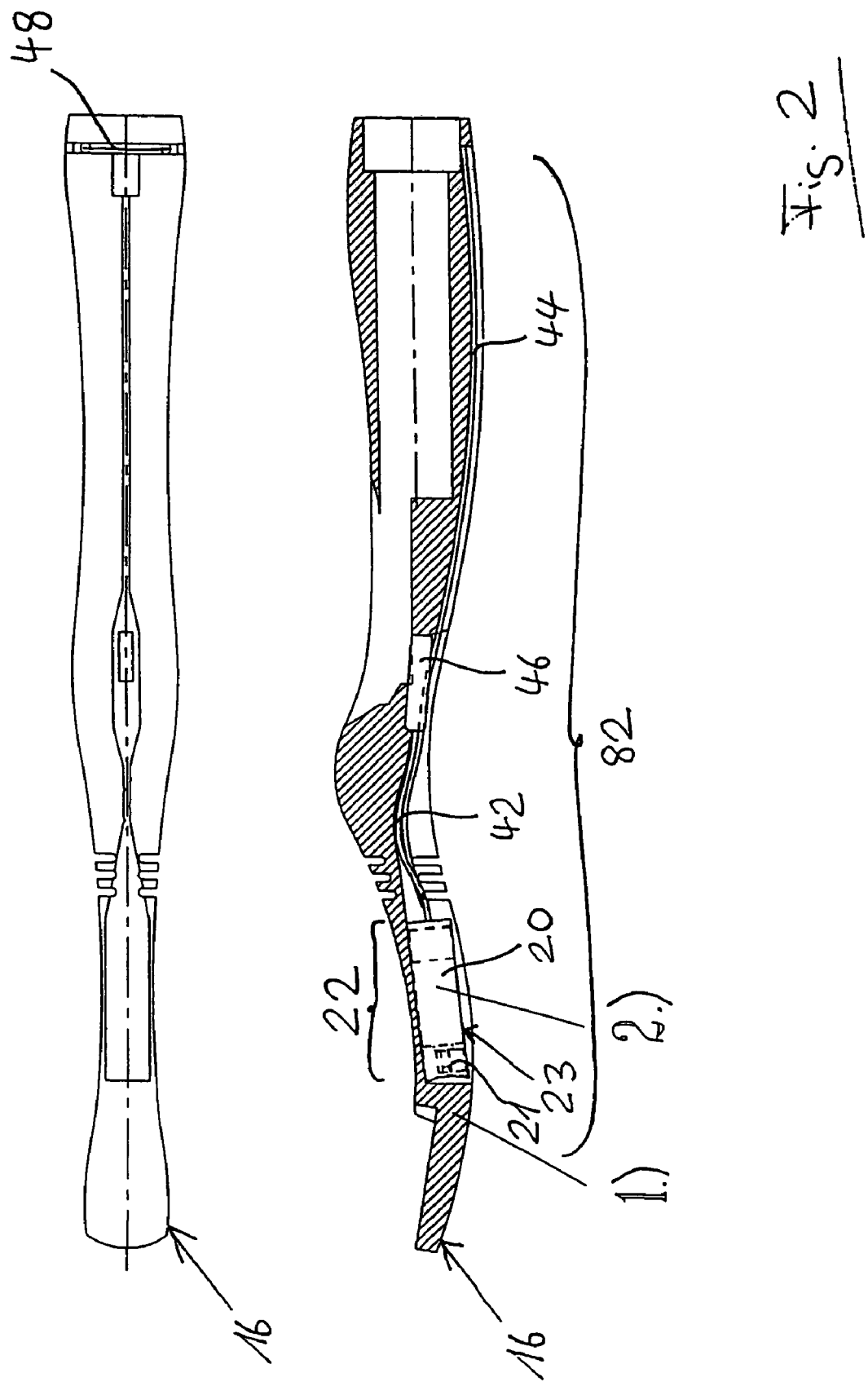

According to FIG. 2, in the next step, a functional subassembly 82, which has previously been put together from individual elements, is fixed on the hard component 16. This subassembly 82 comprises a vibration device 22 with a protective sleeve 23 as well as an electric motor 20 and an eccentric 21 which can be driven by the latter, the electric motor and the eccentric being arranged in the sleeve 23. By means of the vibration device 22, the head region 14 of the toothbrush can be made to vibrate at a frequency of a few 1000 Hz. The sleeve 23 serves, on the one hand, for protecting the vibration device 22 against effects of pressure and temperature of the plastic component which is to be injection molded subsequently and, on the other hand, for keeping the eccentric free of the plastic material of the component. The sleeve 23, which is resistant to injection pressure, is produced from plastic, ceramic material or—preferably—metal. The protective sleeve 23 may alternatively be formed from a plastic of which the melting point is above the temperature of the plastic component which is to be injection molded subsequently. The outer length of the sleeve 23 is approximately 10 to 25 mm, preferably 20.5 mm, while the diameter of the sleeve 23 is approximately 2 to 10 mm, preferably 6.4 mm, and the wall thickness of the sleeve 23, which may be up to 3 mm, is preferably 0.2 mm. Once the eccentric 21 and the motor 20 have been introduced, the sleeve 23 is either closed by means of a cover or filled with a resin. A stop is preferably provided on the sleeve 23, level with the end of the motor 20, as a result of which the eccentric 21 is prevented from advancing too far during assembly.

Two electric connecting lines 42, 44 are connected to the vibration device 22. These connecting lines are preferably provided in the form of a sheathed stranded or single wire made of copper, the wire diameter, which may be up to 1 mm, preferably being 0.3 mm. The thickness of the sheath is in the range from 0.1 to 0.5 mm, preferably 0.2 mm. This means that the sheath is reliably protected against being washed away, so to speak, during the encapsulation by the plastic, with the result that no short circuit can occur even when the electric lines 42, 44 are displaced on account of the injection pressure.

An electric line 42 is of relatively short configuration and extends as far as the through-passage 56 between the widened region of the channel 52 and the central cavity 29 (see FIG. 1). For this purpose, in this exemplary embodiment, the short line 42 is provided with a pin-like or plate-like contact element 46, which is designed as an axial extension of the line 42. Via a switching element which will be described in more detail elsewhere in the text, it is possible for the contact pin 46 to be connected to one pole of an energy store arranged in the rear cavity 28.

For contact-connection to the other pole of the energy store, use is made of the longer connecting line 44, which extends as far as the recess 58 formed in the rear region (see FIG. 1).

The electric lines 42, 44, as constituent parts of the prefabricated subassembly 82, have preferably already been made into the required length in each case. The free ends of the lines 42, 44, furthermore, may already be stripped and tin-plated, which is advantageous, in particular, when—as corresponds to the preferred procedure—force-fitting connections, rather than solder connections, are provided for contact-connection to further electrical functional elements. This will be discussed in more detail hereinbelow.

In order to fix the lines 42, 44 on the hard component 16, the channel 52 between the vibration-damping region 34 and the widened channel region is designed as a labyrinth 54 (see FIG. 1). This retaining region, designed for example as a three-point labyrinth, secures the lines 42, 44 against dropping out and against tension.

The contact pin 46 and the through-passage 56 (see FIG. 1) are coordinated with one another such that the cavity 29 located in the central region is sealed from beneath against the penetration of plastic of the component which is to be injection molded subsequently.

Prior to the injection molding of the next, preferably soft, component, the already mentioned, U-shaped contact clip is introduced, in particular pressed in a force-fitting manner, into the recess 58 formed at the rear end, as a result of which the long connecting line 44 is also fixed at its free end and, moreover, an electrical contact is produced between the free end of the line 44 and the contact clip without a solder connection having to be produced. The contact clip will be discussed in more detail, in conjunction with FIG. 10, elsewhere in the text.

Figure 3:
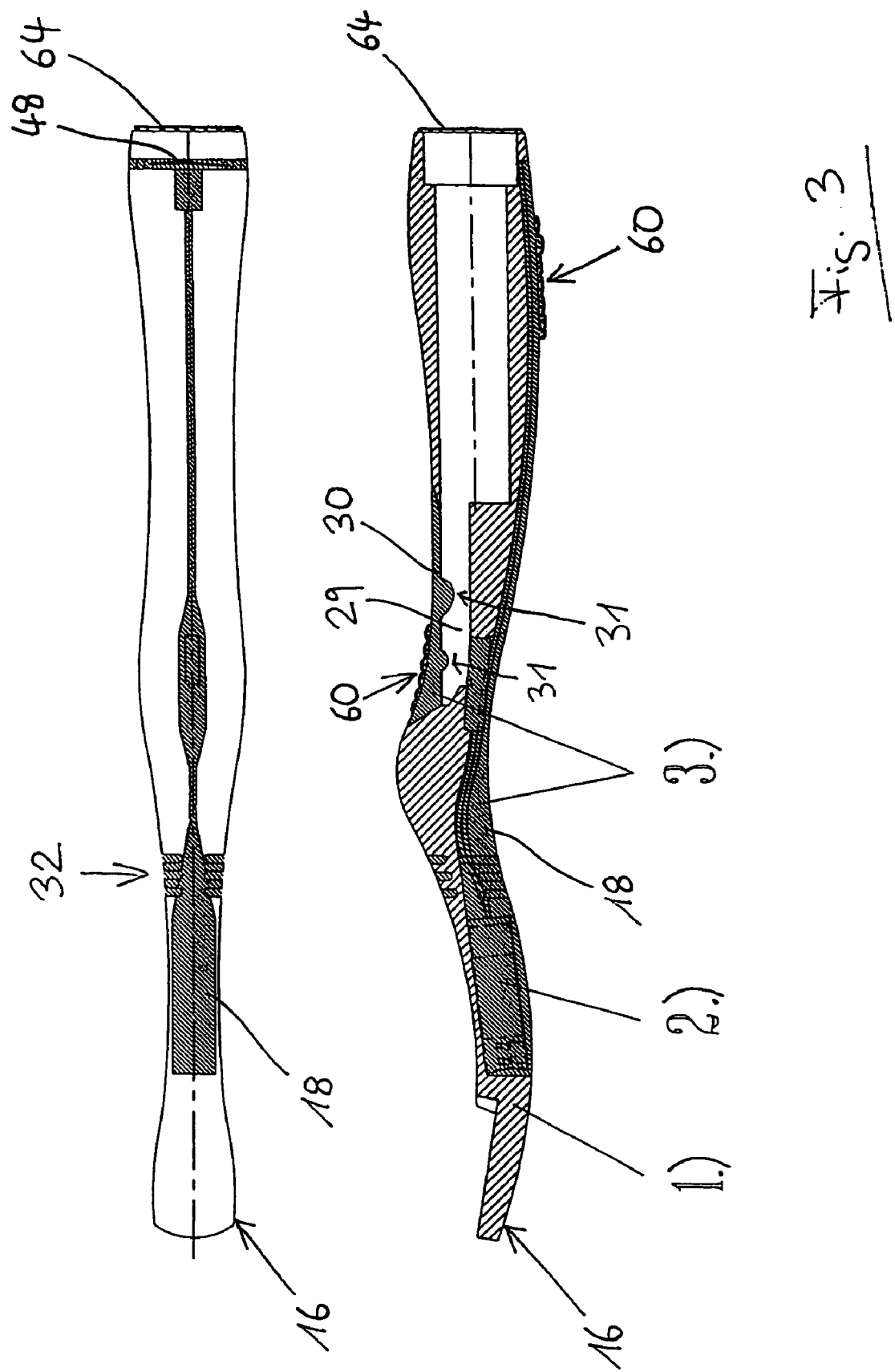

FIG. 3 shows the toothbrush according to the invention following the injection molding of the soft component 18. The injection molding of the soft component 18 takes place in a second cavity of the injection mold, in which the hard component 16 is positioned once it has been fitted with the abovedescribed functional elements (vibration device 22 comprising sleeve 23, eccentric 21 and motor 20, electric lines 42, 44, contact pin 46 and contact clip 48).

The soft component 18 covers over the functional elements arranged on the hard component 16, i.e. the functional elements are encapsulated directly by the plastic which forms the soft component 18.

The cavity 29 provided in the central region is closed in the upward direction by the injection molding of the soft component 18. The flexible plastic of the soft component 18 here forms a switching region 30, which can be pressed into the cavity 29 by actuation from the outside and is provided on its inside with two switching protrusions 31 projecting into the cavity 29. This switching region 30, which is also referred to as a switching membrane, is formed with the aid of a mold core (not illustrated) of the injection mold, the mold core being introduced into the cavity 29 during the injection molding of the soft component 18. The flexible properties of the switching region 30 allows straightforward forced demolding by virtue of the mold core being withdrawn in the rearward direction, as a result of which the compliant switching region 30 is forced outward via the switching protrusions 31 and then, on account of its elasticity, once again assumes the normal position shown in FIG. 3.

The Shore hardness A of the switching region 30 is preferably in the range of from 15 to 70, in particularly approximately 35.

Furthermore, the vibration-damping region 32 is completed by the injection molding of the soft component 18, in that the corresponding recesses 34 (see FIG. 1) of the hard component 16 are filled with the plastic of the soft component 18.

As is indicated in FIG. 3, it is also possible for the injection molding of the soft component 18 to form further functional regions 60, which are preferably designed as additional damping regions in the region of the finger and/or hand rest and may be provided, for example, in the form of ribs, small pads or repeating patterns of basically any desired configuration.

Furthermore, as a result of the injection molding of the soft component 18, an encircling sealing lip 64 is formed on the rearwardly oriented end side of the toothbrush body, the sealing lip allowing a closure cover to be fitted in a water-tight manner, which will be discussed in more detail elsewhere in the text.

The soft component 18 is prevented from penetrating into the central cavity 29 from beneath by the contact pin 46, which is connected to the end of the short electric line 42b (see FIG. 2) and closes the through-passage 56 (see FIG. 1). The contact pin 46 is supported during the injection molding of the soft component by the abovementioned mold core of the injection mold, the mold core being introduced into the cavity.

Figure 4:
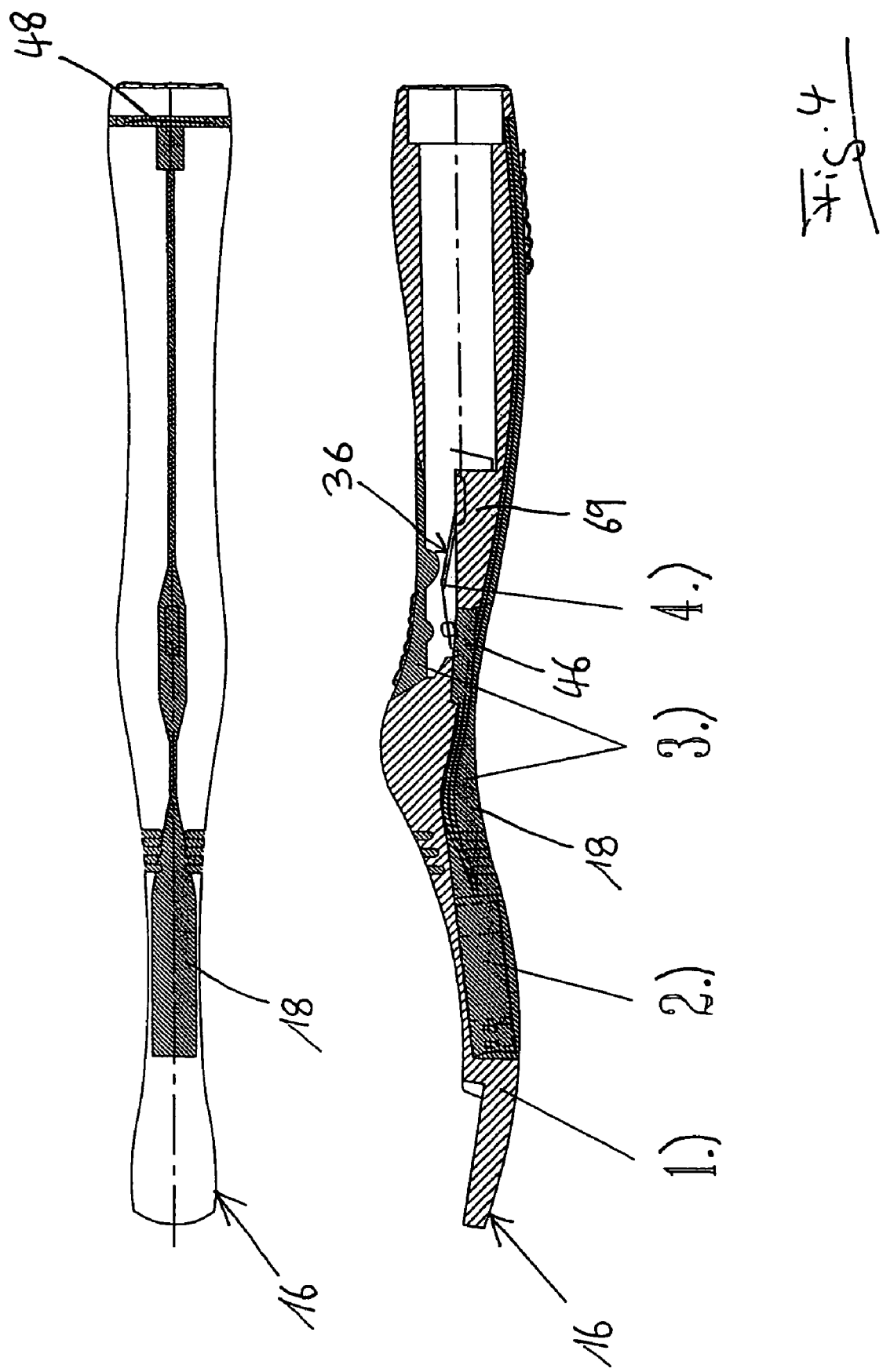

Then, in accordance with FIG. 4, the switching element 36 (butterfly) is introduced into the cavity 29 from the rear. The butterfly 36 is fixed on a carrier section 69 of the hard component 16 simply by being plugged on. This will be discussed in more detail hereinbelow in conjunction with FIG. 9.

Figure 5:
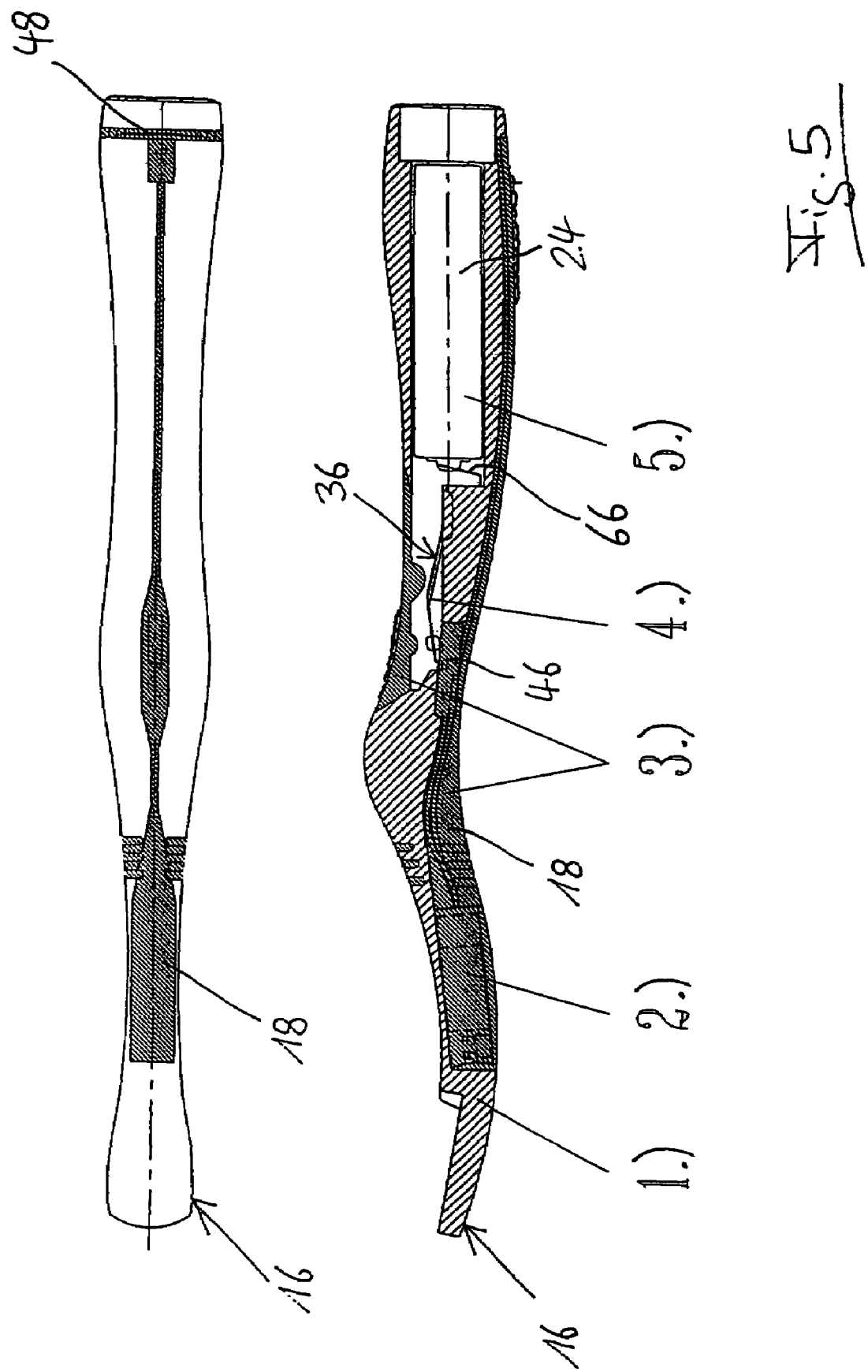

In the next step, according to FIG. 5, a battery 24, in particular a battery of type AAA (1.5 V) is introduced from the rear into the cavity 28 which is provided for this purpose. Use is made as length-compensating means, and for the contact-connection of one battery pole, of a spring section 66 formed at the rear end of the butterfly 36.

Figure 6:
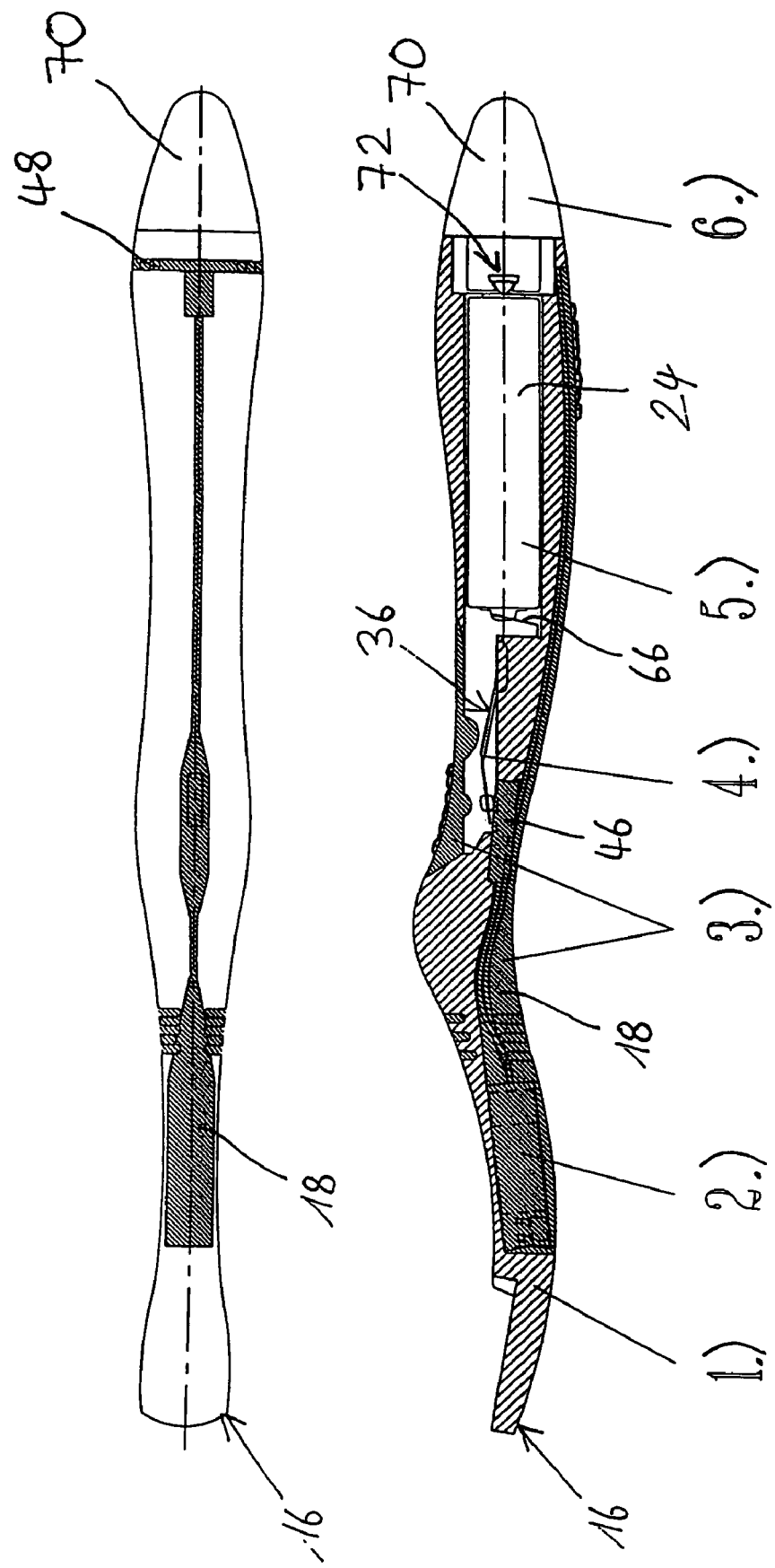

According to FIG. 6, in the next step, a cover 70 is positioned on the rear end of the toothbrush body. The cover 70 is a preassembled subassembly which comprises an electrically conductive contact section 72 via which, in the assembled state, an electrical connection is produced between the other pole of the battery 24, on the one hand, and the contact clip 48, which has previously been inserted into the recess 58 of the hard component 16 (see FIG. 1) and has then been encapsulated by the soft component 18 (see FIG. 3), whereby the electrical connection of all the functional elements concerned is complete.

The connection between the cover 70 and the rear end of the toothbrush body, with the interposition of the sealing lip 64 formed by injection molding the soft component 18 (see FIG. 3), preferably takes place in the manner of a bayonet closure, which will be discussed in more detail in conjunction with FIG. 10 and, in particular, FIG. 13. It is alternatively possible for the connection to take place, for example, by other suitable means, for example by latching.

As FIG. 7 shows, a prefabricated brush head 76 is then fitted. The head 76 may be fastened on the head region 14 of the hard component 16, in principle, by any desired suitable means, for example latching, adhesive bonding or welding, in particular ultrasonic welding.

The abovementioned operation of fitting a completely prefabricated head 76 comprising a platform 78 already provided with the bristles 80 has the advantage that different heads 76 may be fitted on the head region 14 of the hard component 16. It is thus possible for the head 76 which is to be fitted to be alternatively provided with massage elements rather than cleaning elements. A combination of massage and cleaning elements on a head is also possible according to the invention. A concept for exchangeable heads on toothbrushes is described in WO 98/01055 A1 and EP 0 910 258 B.

As an alternative to fitting an already bristle-covered head 76, the toothbrush body produced by plastic injection molding may also be designed, in the head region, such that the cleaning and/or massage elements are fitted directly on the toothbrush body, i.e. the injection-molded toothbrush body is directly covered with bristles.

The bristle-covering operation, i.e. the operation of fitting the head with cleaning and/or massage elements, may take place, in principle, by any desired bristle-covering process (e.g. IMT or AFT).

FIG. 8 shows a variant, which has already been mentioned above, for producing an electrically conductive connection between the short electric line 42 and the switching element (butterfly) 36. Instead of the contact element 46 (see FIG. 2), which is already firmly connected to the free end of the short electric line 42 in the prefabricated state, this variant provides a separate contact pin 46', which, once the prefabricated subassembly 82 has been fitted on the hard component 16 and prior to the injection molding of the soft component 18, is introduced into a recess which, in the case of this variant, is formed during the injection molding of the hard component 16, as a result of which an electrically conductive connection is produced between the contact pin 46' and the free end of the short electric line 42. The switching element 36 may be connected electrically to the short electric line 42 via the contact pin 46'.

Consequently, the insertion of the contact pin 46' in this variant constitutes a further production step (2.1), which takes place together with the already described operation of introducing the U-shaped contact clip 48.

The operation of fixing the contact pin 46', which is necessary during the injection molding of the soft component 18, can take place by means of a special slide of the injection mold, the slide retaining the contact pin 46' securely in position. This retaining device may be a controlled slide which, during the injection-molding operation, is moved into an operating position and presses the contact pin 46' with sealing action, counter to the force of the inflowing plastic mass, against the boundary of the through-passage 56 in relation to the top cavity 29 and/or against a wall which separates the top cavity 29 from the accommodating region of the hard component 16, which is located therebeneath, and has an opening for the contact pin 46'. The contact pin 46' may be supported during the injection molding of the soft component 18 by means of the abovementioned mold core arranged in the cavity 29.

The contact pin 46', however, is preferably fixed not by a slide, but simply by being pressed in a force-fitting manner. For this purpose, the contact pin 46' may be provided with retaining means, e.g. in the form of knurling, surface roughening or a rear-engagement means, as a result of which an effective force-fitting connection is easier to produce. Correspondingly, it is preferably also the case that the contact clip 48 is introduced into the recess 58, and fixed, by being pressed in a force-fitting manner.

Using the separate contact pin 46' is preferred to using a contact pin 46 which is firmly connected to the short electric line 42.

FIG. 9 shows in the bottom part, on an enlarged scale, the region of the toothbrush body in which the switching element (butterfly) 36 is arranged. The butterfly 36 has two legs 40 which are connected to one another in an articulated manner at an articulation region 38. The leg 40 which is on the left-side in FIG. 9 serves for the contact-connection of the separate contact pin 46' explained above (see FIG. 8) or of the integrated contact pin 46 (see, in particular, FIGS. 2 and 4), it being possible for the relevant leg 40 of the butterfly 36 to be modified for this purpose, as can be gathered, for example, from FIG. 4.

The other leg 40 of the butterfly 36 is provided, at its end, with a plug-in section 68, by means of which the butterfly 36 is pushed over a cross-sectionally dovetail-like carrying section 69 of the hard component 16 (see the enlarged detail on the right-hand side of FIG. 9), as a result of which the butterfly 36 is fixed on the toothbrush body. The plug-in section 68 of the butterfly 36 is adjoined by the already mentioned spring section 66 for the contact-connection of one pole of the battery 24.

By virtue of the legs 40 being activated via the switching protrusions 31 formed on the switching membrane 30, it is possible for the butterfly 36 to be changed over between two dimensionally stable states in order thus to switch the toothbrush on and off. For example, starting from the on state illustrated in FIG. 9, activation of the leg 40 on the right-hand side of FIG. 9 moves the articulation region 38 downward, as a result of which the butterfly 36, as from a certain press-in depth, abruptly changes over and the leg 40 on the left-hand side of FIG. 9 springs upward and thus breaks contact with the contact pin 46' or 46. The same applies to activation of the leg 40 on the left-hand side of FIG. 9 for the purpose of switching the toothbrush on. The abrupt changeover of the butterfly 36 is assisted by arms 67 which run parallel to the leg 40 on the right-hand side of FIG. 9 and are connected to the other leg 40, on the left-hand side of FIG. 9.

The enlarged detail illustrated on the left-hand side of FIG. 9 shows, in particular, the electrical connection, produced by means of the contact pin 46', between the free end of the short electric line 42 and the leg 40 of the butterfly 36. It is also possible to see the long electric line 44, which has been guided past the head of the contact pin 46'.

FIG. 10 shows a side view and a plan view of the rear end of the toothbrush body. The plan view, illustrated on the right-hand side, shows, in particular, the position of the recess 58 provided for the U-shaped contact clip 48, while the side view, illustrated on the left-hand side, shows how, by means of the contact clip 48 introduced into the recess 58, an electrical connection is produced between the free end of the long electric line 44 and the contact section 72 of the cover 70, which is not otherwise illustrated here (see FIG. 6).

The contact section 72 of the cover 70 comprises a contact head 73, for the contact-connection of the battery 24, and a contact tongue 74, which projects radially beyond a cylindrical carrying section 71 (see FIG. 13), by means of which the contact section 72 is retained, and which serves, on the one hand, for the contact-connection of the contact clip 48 and, on the other hand, for locking the cover on the toothbrush body in the manner of a bayonet closure, in that the contact tongue 74 engages behind the legs of the U-shaped clip 48.

Both by means of the separate contact pin 46' (see FIGS. 8 and 9) and by means of the separate contact clip 48, the necessary electrical connections are consequently produced without soldering, which simplifies the production process for the toothbrush according to the invention to a considerable extent.

Figure 11:
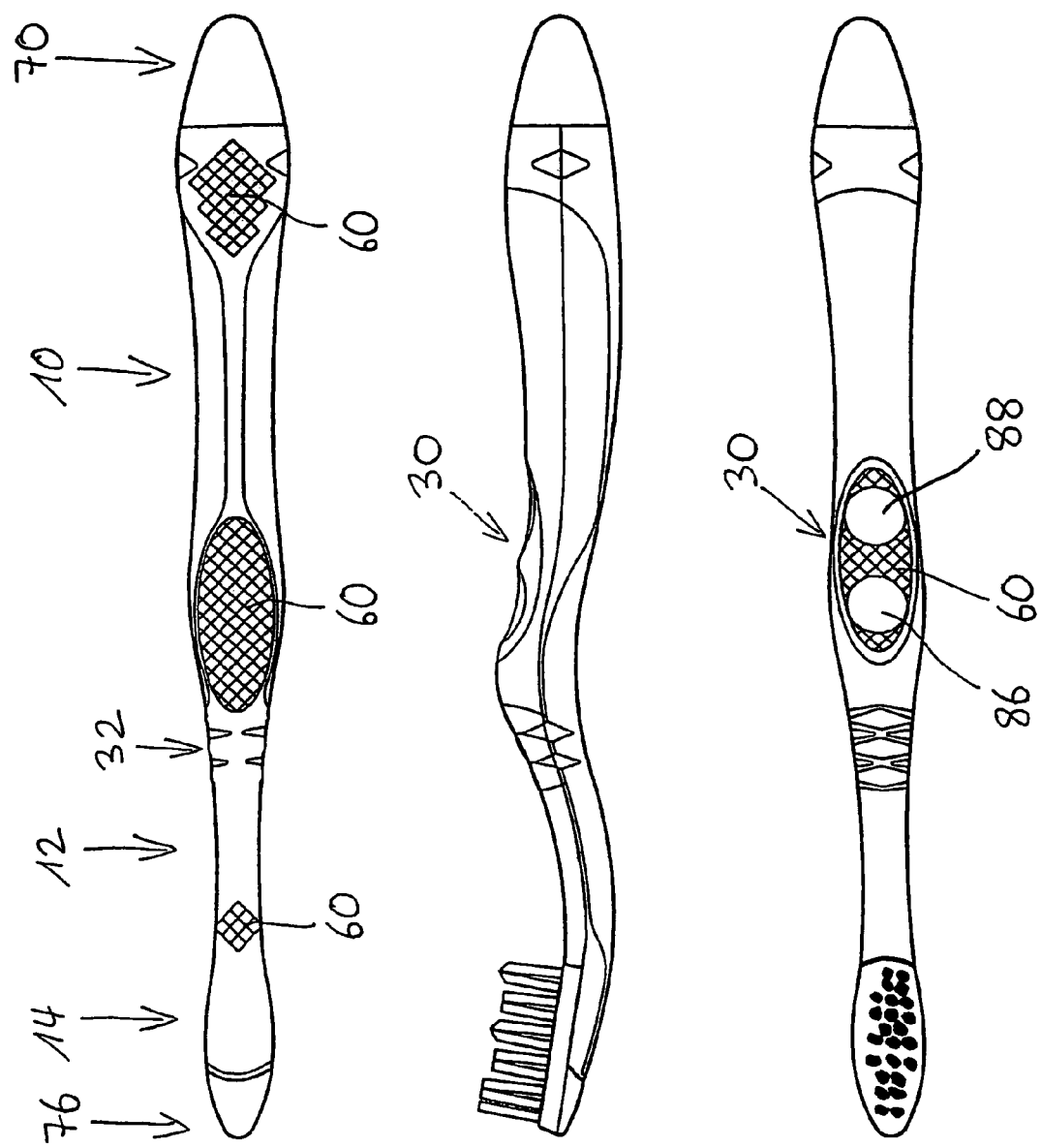
FIG. 11 shows various views of a completed toothbrush according to the invention.

FIG. 11 shows various views of a preferred design of a toothbrush according to the invention produced by the process of the invention. The top, rear view contains functional regions 60 which are produced, in particular, by injection molding of the soft component 18 and, apart from being a design feature, serve for vibration damping and/or ensure a particularly good grip of the toothbrush according to the invention.

In the example illustrated, the functional regions 60, which serve in part as a hand or finger rest, are located on the rear side (i) in the region of the transition between the head region 14 and the neck region 12, (ii) in the handle region 10 level with an intermediate region between the vibration-damping region 32 and the switching region 30, and (iii) in the region of the rear end of the handle region 10. A further functional region 60 encloses the two switching points 86 on the front side.

Also visible in FIG. 11 is the vibration-damping region 32, formed by the hard component and the soft component together, in the region of the transition between the handle region 10 and neck region 12, the vibration-damping region, in this preferred design example, having a lattice-like geometry. Particularly good torsional, flexibility and damping properties can be achieved by such a configuration.

The bottom plan view shows, in particular, the switching region 30, formed by the injection-molded soft component, with the two switching points 86, 88 for switching the toothbrush on (switching point 86) and off (switching point 88).

As can be gathered from the illustrations of FIG. 11, the toothbrush according to the invention—although an electrically operated toothbrush—is shaped in a pleasing and elegant manner without any disruptive thickened portions or awkward regions. In particular, the toothbrush according to the invention is provided with a curved neck region 12, which is particularly attractive from an aesthetic point of view. Such a slim design is made possible by the production process according to the invention, without this resulting in concessions having to be made as regards outlay and the amount of time required for producing the toothbrush.

Figure 12A:
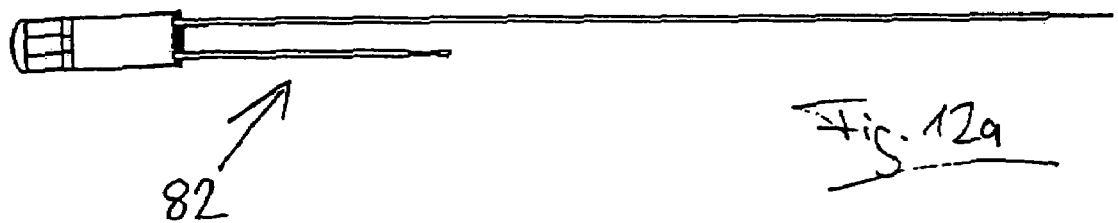
FIGS. 12a and 12b show possible embodiments of a prefabricated subassembly of functional elements for a toothbrush according to the invention.
Figure 12B:
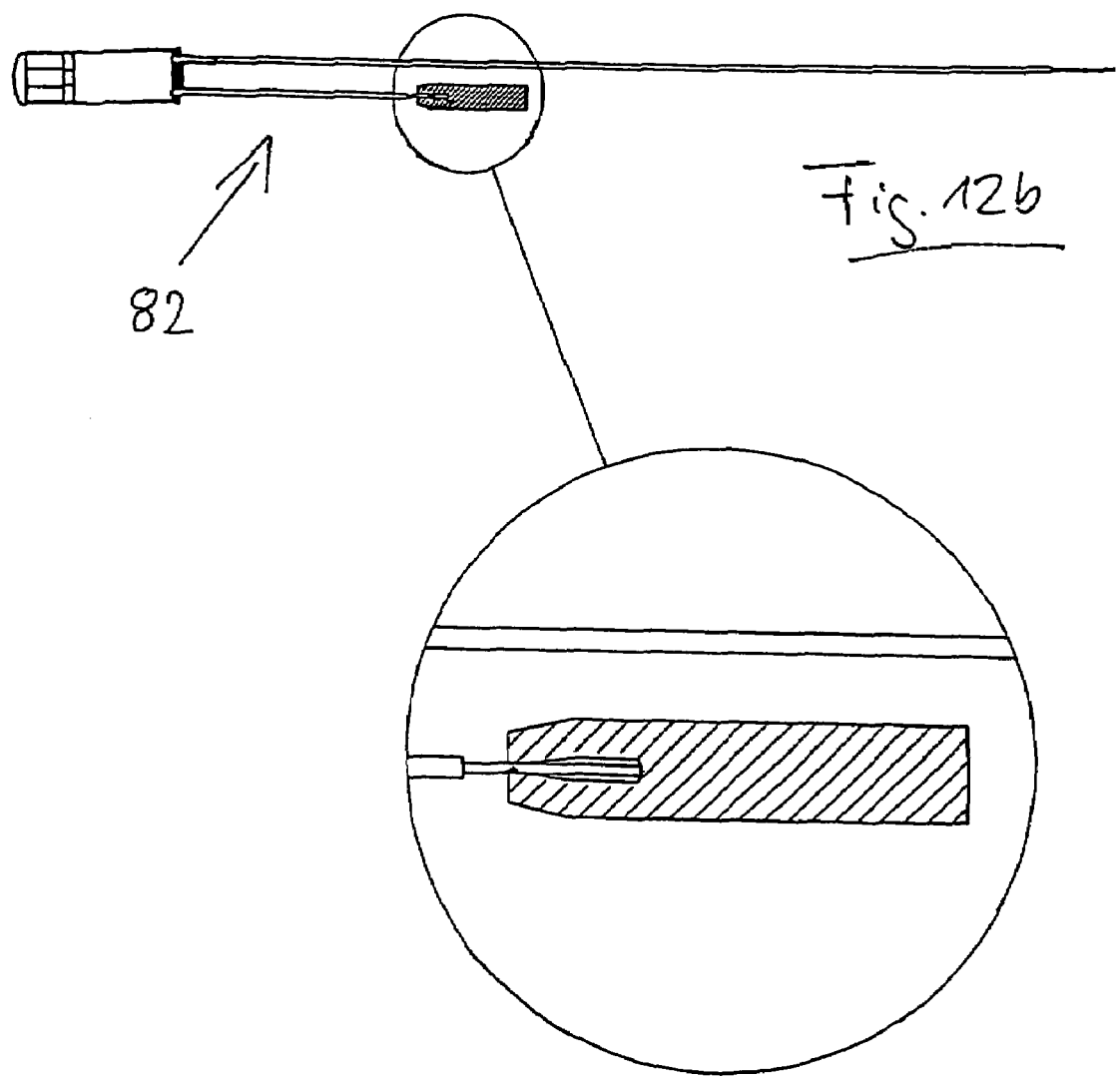

FIGS. 12a and 12b each show the prefabricated subassembly 82 which, in the abovedescribed exemplary embodiment, is arranged on the previously injection-molded hard component 16 prior to the injection molding of the soft component 18 (see FIG. 2). In this case, FIG. 12a shows the preferred variant without a contact pin fitted at the free end of the short electric line 42, i.e. this variant is used in conjunction with the separate contact pin 46' explained above (see, in particular, FIG. 8), while FIG. 12b shows the variant illustrated in FIGS. 2-7, with a contact pin 46 soldered on the electric line 42.

In both cases, the vibration device 22 comprises the protective sleeve 23, in which the eccentric 21 and the motor 20 are arranged and which is filled with a resin once the functional elements have been introduced.

Figure 13:
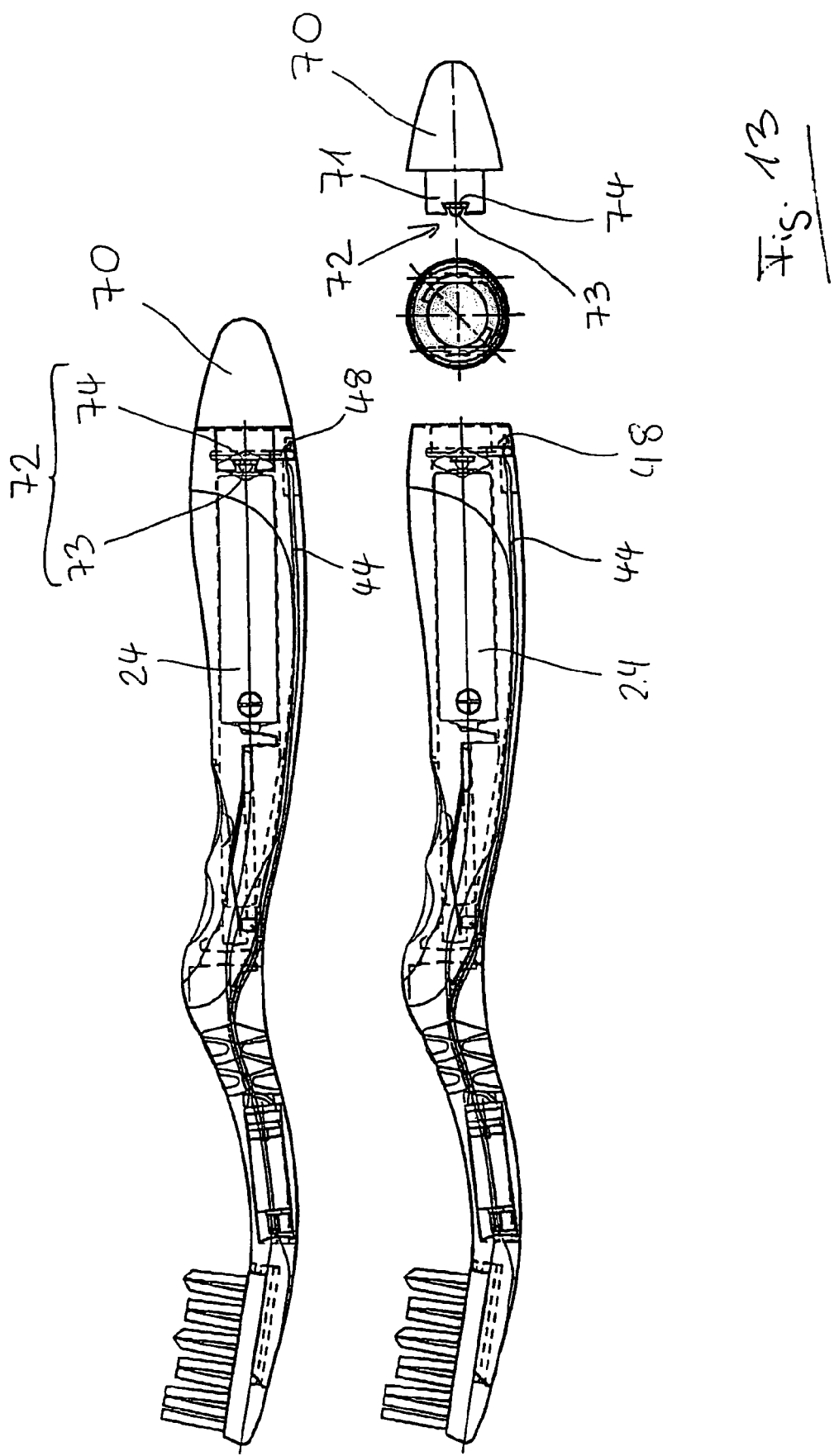
FIG. 13 shows illustrations of a toothbrush according to the invention in order to explain the locking of a cover.

FIG. 13 shows, in the top illustration, the toothbrush according to the invention in a state in which it has been closed by means of the cover 70, while the bottom illustration shows the toothbrush according to the invention before it is closed by means of the cover 70.

As has already been mentioned in conjunction with FIG. 10, in the exemplary embodiment illustrated, the cover 70 is locked on the toothbrush body by a bayonet closure. For the purpose of closing the toothbrush, the cover 70 is positioned in relation to the toothbrush body at an angle at which the contact tongue 74 of the contact section 72 of the cover 70, the contact tongue projecting radially at mutually opposite locations in relation to a cylindrical carrying section 71 of the cover 70, is inclined in relation to the legs of the U-shaped contact clip 48 such that the contact tongue 74 is introduced into the toothbrush body, past the legs, and the contact head 73 can come into contact with the rear pole of the battery 24. By virtue of the cover 70 then being rotated in relation to the toothbrush body, for example through 90° in the clockwise direction (as seen from the rear), the contact tongue 74 engages behind the legs of the U-shaped contact clip 48 by way of its two radially projecting end sections. As a result, on the one hand, the cover 70 is securely locked and, on the other hand, the electrical contact is produced between the contact tongue 74 and the contact clip 48 and thus between the long electric line 44, the contact head 73 and the battery 24.

Figure 14:
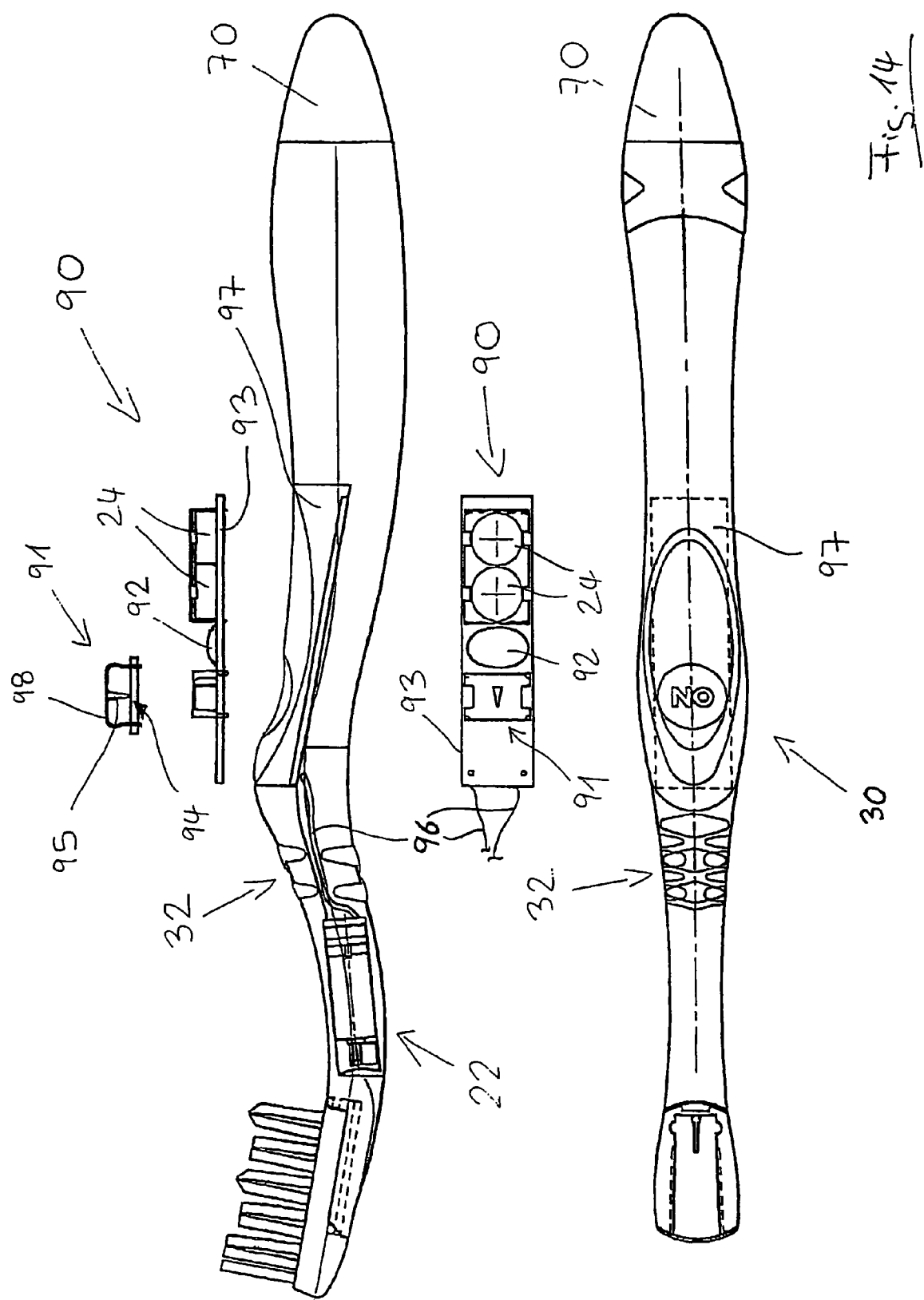
FIG. 14 shows various views of a further embodiment of a toothbrush according to the invention.

FIG. 14 shows a further embodiment of a toothbrush according to the invention, in the case of which a control unit 90 is provided for the vibration device 22, the control unit, following the injection molding of the hard component, being arranged in an accommodating region 97 of the hard component and then being encapsulated or overmolded as a whole by the soft component.

The control unit 90 comprises a carrier 93 which is designed, in particular, as a printed circuit board and on which are arranged two batteries 24, for example commercially available button cells (1.5 V), an integrated circuit 92 and a switch 91, which is also illustrated separately on an enlarged scale in FIG. 14.

In the preferred variant illustrated, the switch 91 is a pulse switch by means of which a switching operation is triggered whenever the free, pointed end of an electrically conductive, spike-like switching element 95 comes into contact with an electrically conductive mating contact 94 on the carrier or the printed circuit board 93.

The switching operations are triggered in each case by virtue of an electrically conductive, deformable mount 98, on which the switching element 95 is fastened and which is fitted on the carrier 93, being pressed down.

The switch 91 is designed such that, during the injection molding of the soft component, the space within the mount 98 which encloses the switching element 95 is also filled with the plastic material of the soft component. As a result, the interspace between the free contact end of the switching element 95 and the mating contact 94, the interspace corresponding to the switching distance of the switch 91, is filled with plastic. When the switch 91 is actuated for the first time, this material is pierced by the contact spike 95 and a first switching operation is triggered. The switching element 95 is restored automatically on account of the elasticity of the soft component, i.e. the operation of the switching element 95 being pressed downward via the mount 98 in order to trigger a switching operation takes place counter to the restoring force of the soft component.

The vibration device 22, the construction of which corresponds to the previously described vibration device, is connected to the control unit 90 via supply lines 96. The integrated circuit 92 may be designed in order to realize the wide range of different control functions. It is thus possible to provide, for example, that the action of triggering successive switching operations by means of the switch 91 alternately switches the vibration device 22 on and off. It may alternatively be provided, for example, that the vibration device 22 is switched on by single actuation of the switch 91 and the circuit 92 ensures that the vibration device 22, following a predetermined period of time, is switched off automatically without the switch 91 having to be actuated again for this purpose.

In an alternative configuration, it is possible for the batteries 24 to be arranged separately from the control unit 90 and to be positioned, for example, to the rear of the handle region and be connected to the control unit 90 via additional supply lines.

The toothbrushes described above with reference to FIG. 14 are preferably designed as disposable brushes which are disposed of once the batteries 24 have been used up. It is alternatively possible for the toothbrush to be configured with a removable cover section, via which the batteries 24 are accessible and can be exchanged in order, in this way, for it to be possible to use the toothbrush more frequently.

In the embodiment illustrated in FIG. 14, the switching region 30 for actuating the switch 91 is provided in the region of the thumb rest of the toothbrush. In an alternative variant, it is also possible for the switching region to be arranged in the region of the rear end of the toothbrush and to be integrated, for example, in the rear end section of the toothbrush body or in the cover 70. It is further possible according to the invention for the cover 70 to be designed as a rotary switch and to have to be rotated through a predetermined angle range in relation to the toothbrush body in order to trigger a switching operation.

In a further alternative configuration, in contrast to the embodiment according to FIG. 14, the vibration device 22 may be fitted directly on the carrier 93 of the control unit 90. This configuration, on the one hand, would also result in vibrations in the handle region, but on the other hand it would advantageously be possible to dispense with supply lines between the vibration device 22 and control unit 90.

It is preferred for the vibration device 22 to be positioned in the vicinity of the toothbrush head according to FIG. 14, the vibration-damping region 32 preventing vibrations in the handle region of the toothbrush.

The further alternative embodiment of a toothbrush according to the invention which is shown in FIG. 15 corresponds essentially to the embodiment of FIG. 14, the one difference being that, instead of a vibration device 22, another functional element is connected to the control unit 90, namely an illuminating device 22' in the form of an LED. It should be expressly pointed out here that the illuminating device 22' according to FIG. 15 merely constitutes a preferred example of a further functional unit, and it is alternatively also possible to provide the functional unit in the form of a sensor designed for the respectively desired use purpose.

The light source 22', which is encapsulated by a soft component, may be a light source which can be switched on and off as required, is permanently active in the switched-on state and is intended for illuminating the oral cavity. The light source 22' may alternatively be used as a timer which, after having been switched on for a period of, for example, two minutes, flashes and is then switched off automatically. An alternative or additional function may consist in the light source 22' being used as an indicator to inform the user that the service life of the toothbrush is coming to an end, in that, for example following a predetermined number of e.g. 200 switching-on operations, the light source 22', for example, no longer illuminates at all, is operated at a different flashing frequency or is permanently illuminated, i.e. the end of the service life is indicated by the light source 22' operating in a state which differs from the normal operating state.

As in the case of the embodiment according to FIG. 14, all the electrical components are connected to the carrier 93, which, following the injection molding of the basic-body-forming hard component of the toothbrush, is fixed on the basic body by anchoring means.

In contrast to the illustration in FIG. 15, the light source 22' may be fitted directly on the carrier 93. The gap between the free end of the switching element 95 and the mating contact 94, the gap constituting the switching distance for the switching element 95, is preferably less than 5 mm. The mount 98, which bears the switching element 95 and is preferably produced from metal, e.g. spring steel, brass or copper, preferably has a material thickness of at least 0.5 mm, in order to prevent deformation on account of the injection pressure.

The batteries 24 are preferably anchored on the carrier plate 93 by injection welding, with the result that, during the injection molding of the soft component, the electrical contact between the batteries 24 and the carrier plate 93 is reliably maintained. In dependence on the power/voltage values which are required in each case, it is possible for one or more batteries 24 to be fitted in parallel or in series.

The integrated circuit 92 is preferably covered by a layer of resin, in order to provide protection against the heat and the pressure during the injection molding of the soft component, which is formed from an elastomeric or flexible material.

What has been said above in relation to the control unit 90 applies correspondingly to the control unit 90 of the embodiment which is illustrated in FIG. 14 and comprises a vibration device 22 instead of a light source 22'.

If a light source 22' is used as the functional unit, it is preferred for a transparent or translucent elastomeric or flexible material to be used as a soft component, this material allowing the radiation emitted by the radiation source 22' to pass as far as possible without obstruction.

As a comparison of FIGS. 14 and 15 shows, one difference between the two toothbrushes according to the invention is that the variant with light source 22' has dispensed with the formation of a vibration-damping region 32, which, in the case of the variant with vibration device 22, is provided in the region of the transition between the handle region and neck region of the toothbrush.

FIG. 16 shows an example of a placement pallet 84, which is used in the largely automated production of the toothbrush according to the invention. By means of this pallet 84, the prefabricated subassemblies 82 (see, in particular, FIG. 12b) are supplied such that the subassemblies 82 can be easily removed, by a machine, from the depressions provided in the pallet 84.

FIG. 17 shows, merely schematically, a plan view of an assembly installation which is used for the production according to the invention of the toothbrush designed according to the invention and by means of which largely automated handling and assembly/fitting of the individual components and elements can take place. It is possible here to provide both a rotary-table and a transfer-installation arrangement. Use is made of two or more injection-molding machines, which are preferably provided with vertical subassemblies for injection molding the hard component and/or the soft component of the toothbrush body.

In a preferred configuration, one or two rotary-table and/or transfer-installation arrangements are provided, while 4, 6 or 8 injection-molding machines are provided, since the cycle time which is required for the injection molding is longer than the cycle time of the rotary-table and/or transfer-installation arrangement.

The production steps according to FIG. 17, in which—apart from the separate contact pin 46' being used instead of the preassembled contact pin 46—the numbering used here also corresponds to the production step numbering specified in FIGS. 1-8, are as follows:

1. Injection molding the hard component 16
2. Positioning the prefabricated subassembly 82 in the hard component 16
    2.1 Pressing in the contact pin 46'
3. Injection molding the soft component 18
4. Fitting the switching element (butterfly) 36
    4.1 Carrying out a performance test
5. Fitting the battery 24
    5.1 Preassembling the closure cover 70
6. Fitting the closure cover 70
7. Fitting the prefabricated brush head 76
8. Packaging In contrast to the procedure described with reference to FIG. 17, it is also possible, in particular in dependence on the actual configuration of the toothbrush, to provide the production steps in a different order. Furthermore, it is possible for some of these production steps to be dispensed with, which is the case in particular with the disposable variant described with reference to FIGS. 14 and 15, in the case of which, for example, the above-cited step 5 of inserting the battery is dispensed with.

The present application claims priority to German Application No. 102 45 086.2, filed on Sep. 27, 2002, the disclosure of which is herein expressly incorporated by reference in its entirety.

While the invention has been described with reference to exemplary embodiments thereof, it is to be understood that the invention is not limited to the disclosed embodiments or constructions. To the contrary, the invention is intended to cover various modifications and equivalent arrangements. In addition, while the various elements of the embodiments are shown in various combinations and configurations, which are exemplary, other combinations and configurations, including more, less or a single element, are also within the spirit and scope of the invention.

What is claimed is:

1. A process for producing an oral care device having a body, which comprises a handle region, a head region and a neck region located between the handle region and the head region, and having electrically functional elements which are arranged, at least in part, within the body and comprise an electrically operated functional unit and an electric supply device which has an energy store for the functional unit, wherein the body is produced, by injection molding, from at least one first component, which serves as a reinforcement, and at least one second component that is softer than the first component, and during the injection molding process of the second component, at least some of the electrically functional elements are encapsulated, at least in part, directly by the plastic which forms the second component and the first component and are arranged in a boundary zone between the first component and the second component.

2. The process as claimed in claim 1, wherein at least one of the encapsulated electrically functional elements encapsulated is a vibration device.

3. The process as claimed in claim 1, wherein at least one of the electrically functional elements encapsulated is a sensor.

4. The process as claimed in claim 1, wherein at least one of the electrically functional elements encapsulated is an illuminating device which has at least one light source.

5. The process as claimed in claim 1, wherein at least one of the electrically functional elements encapsulated is an injection-molded, electrically conductive plastic.

6. The process as claimed in claim 1, wherein at least one of the electrically functional elements encapsulated is a metal switching element.

7. The process as claimed in claim 1, wherein at least one of the electrically functional elements encapsulated is a battery.

8. The process as claimed in claim 1, wherein at least some of the electrically functional elements are provided with a protective sheet or resin before the injection molding process of the second component.

9. The process as claimed in claim 1, wherein first of all the first component is injection molded without the electrically functional elements and then at least some of the electrically functional elements are positioned, and fixed, on the first component, the unit comprising the first component and at least one of the electrically functional elements subsequently being encapsulated, at least in part, by the second component.

10. The process as claimed in claim 1, wherein, prior to the injection molding of the first component, at least some of the electrically functional elements are positioned in an injection mold, and are then encapsulated by the first component, the unit comprising the first component and the encapsulated electrically functional elements subsequently being encapsulated by the second component.

11. The process as claimed in claim 1, wherein, for the second component, first of all, in a first step, the electrically functional elements are covered over at a low injection pressure and then, in a further step, the second component is completed at a high injection pressure.

12. The process as claimed in claim 10, wherein, for the first component, first of all, in a first step, the electrically functional element are covered over at a low injection pressure and then, in at least one further step, the first component is completed at a high injection pressure.

13. The process as claimed in claim 1, wherein at least some of the electrically functional elements are arranged on the already injection-molded first component, such that the arranged electrically functional elements, in relation to a direction of flow of the second component, which is to be injection molded, are located, at least in certain regions, in the shadow of at least one protective section of the first component.

14. The process as claimed in claim 1, wherein at least some of the electrically functional elements or a subassembly of the electrically functional elements which extends over a considerable part of the length of the body is encapsulated.

15. The process as claimed claim 1, wherein the first component is provided, during injection molding, with a retaining or fixing region for one or more electric lines.

16. The process as claimed in claim 1, wherein, prior to the injection molding of the second component, at least one further electrically functional element which is to be encapsulated is fixed at the unit comprising the first component and the electrically functional elements which are to be encapsulated.

17. The process as claimed in claim 1, wherein at least one cavity of the first component, provided for one or more electrically functional elements which are to be inserted at a later stage, is sealed in relation to a further component by at least one electrically functional element which is encapsulated by the first component or is to be encapsulated by the second component or is to be encapsulated by the first component and by the second component.

18. The process as claimed in claim 1, wherein injection molding the second component forms an actuating region, which can be pressed into a cavity of a previously injection-molded first component for the purpose of actuating at least one electrically functional element.

19. The process as claimed in claim 1, wherein a vibration-damping region of the body is formed from at least two different injection-molded components.

20. The process as claimed in claim 10, wherein the first component is a hard plastic component and the second component is a soft plastic component.

21. The process as claimed in claim 1, wherein the first component is a hard plastic component and the second component is a soft plastic component.

22. The process as claimed in claim 19, wherein the vibration-damping region of the body is located either in the neck region or in a region of a transition between the neck region and the handle region.

23. The process as claimed in claim 1, wherein the oral care device is a toothbrush.

24. A process for producing an oral care device having a body with functional elements which are arranged, at least in part, within the body and comprise an electrically operated functional unit and a battery to supply the unit, wherein the body is produced, by injection molding, from at least one first component, which serves as a reinforcement, and at least one second component that is softer than the at least one first component, and during the injection molding process of the second component, the battery is encapsulated, at least in part, directly by the second component and the first component and is arranged in a boundary zone between the first component and the second component.

25. A process for producing an oral care device having a body with electrically functional elements which are arranged, at least in part, within the body and comprise an electrically operated functional unit and a metal switch, wherein the body is produced, by injection molding, from at least one first component, which serves as a reinforcement, and at least one second component that is softer than the at least one first component, and during the injection molding process of the second component, the metal switch is encapsulated, at least in part, directly by the second component and the first component and at least some of the electrically functional elements are arranged in a boundary zone between the first component and the second component.

26. A process for producing an oral care device having a body with functional elements which are arranged, at least in part, within the body and comprise an electrically operated functional unit and one or more electric lines, wherein the body is produced, by injection molding, from at least one first component, which serves as a reinforcement and providing retaining or fixing regions for the electric lines within the first component, and at least one second component that is softer than the at least one first component, and during the injection molding process of the at least one second component, the electric lines are encapsulated, at least in part, directly by the second component and the first component and at least some of the electrically functional elements are arranged in a boundary zone between the first component and the second component.

27. A process for producing an oral care device having a body, which comprises a handle region, a head region and a neck region located between the handle region and the head region, and having electrically functional elements which are arranged, at least in part, within the body and comprise an electrically operated and an electric supply device which has an energy store and is intended for the functional unit, wherein the body is produced, by injection molding, from at least one first component, which serves as a reinforcement, and at least one second component that is softer than the first component, and during the injection molding process of the second component, at least some of the electrically functional elements are encapsulated, at least in part, directly by the plastic which forms the at least one second component and the first component, and at least one cavity of the first component, provided for one or more of the electrically functional elements which are to be inserted at a later stage, is sealed in relation to a further component by at least one of the electrically functional elements which is encapsulated by the first component or is to be encapsulated by the second component or is to be encapsulated by the first component and by the second component and at least some of the electrically functional elements are arranged in a boundary zone between the first component and the second component.

28. The process as claimed in claim 27, wherein at least one of the electrically functional elements encapsulated is an integrated circuit.

29. The process as claimed in claim 27, wherein at least one of the electrically functional elements encapsulated is a position determining device.

30. The process as claimed in claim 27, wherein at least one of the electrically functional elements encapsulated is a switching device.

31. A process for producing an oral care device having a body, which comprises a handle region, a head region and a neck region located between the handle region and the head region, and having electrically functional elements which are arranged, at least in part, within the body and comprise an electrically operated functional unit and an electric supply device which has an energy store and is intended for the functional unit, wherein the body is produced, by injection molding, from at least one first component, which serves as a reinforcement, and at least one second component that is softer than the first component, and during the injection molding process of the second component, at least some of the electrically functional elements are encapsulated, at least in part, directly by the plastic which forms the second component and the first component and are arranged in a boundary zone between the first component and the second component, wherein functional regions are formed by the second component in the handle region.

32. The process as claimed in claim 31, wherein the functional regions form a damping region that dampens vibrations in the handle region.

33. The process as claimed in claim 32, wherein the functional regions are provided at one or more finger or hand rest portions in the handle region.

34. The process as claimed in claim 31, wherein the handle region has a central internal cavity and a through-passage that communicates with an exterior of the handle region, and during injection molding a mold core is inserted into the central internal cavity to support a contact pin that closes the through-passage and prevents penetration of the second component into the central internal cavity.

* * * * *